US007914456B2

(12) United States Patent
Osaka et al.

(10) Patent No.: US 7,914,456 B2
(45) Date of Patent: Mar. 29, 2011

(54) ULTRASONIC PROBE AND ULTRASONIC ELASTICITY IMAGING DEVICE

(75) Inventors: Takashi Osaka, Matsudo (JP); Takeshi Matsumura, Kashiwa (JP); Tetsuya Hayashi, Kashiwa (JP); Mitsuhiro Oshiki, Kamagaya (JP); Okinori Yuasa, Funabashi (JP); Naoyuki Murayama, Kashiwa (JP); Tsuyoshi Shiina, Tsukuba (JP); Satoshi Tamano, Kashiwa (JP); Tsuyoshi Mitake, Noda (JP)

(73) Assignee: Hitachi Medical Corporation, Tokyo (JP)

( * ) Notice: Subject to any disclaimer, the term of this patent is extended or adjusted under 35 U.S.C. 154(b) by 91 days.

(21) Appl. No.: 10/558,642

(22) PCT Filed: May 31, 2004

(86) PCT No.: PCT/JP2004/007856
§ 371 (c)(1),
(2), (4) Date: Nov. 30, 2005

(87) PCT Pub. No.: WO2004/105615
PCT Pub. Date: Dec. 9, 2004

(65) Prior Publication Data
US 2007/0032726 A1 Feb. 8, 2007

(30) Foreign Application Priority Data

May 30, 2003 (JP) .................................. 2003-154349
Jun. 23, 2003 (JP) .................................. 2003-178685
Oct. 14, 2003 (JP) .................................. 2003-354231

(51) Int. Cl.
*A61B 8/00* (2006.01)
(52) U.S. Cl. ........ 600/447; 600/437; 600/439; 600/459; 600/462; 600/467; 601/2

(58) Field of Classification Search .................. 600/437, 600/439, 447, 459, 462, 466, 467, 470, 472; 128/660; 601/2
See application file for complete search history.

(56) References Cited

U.S. PATENT DOCUMENTS
4,545,385 A * 10/1985 Pirschel ........................ 600/445
(Continued)

FOREIGN PATENT DOCUMENTS
DE 199 36 554 2/2001
(Continued)

OTHER PUBLICATIONS

Naotaka Nitta et al. "Choonpa ni yoru Soshinki no Hisenkel Dansei Tokusei no Gozoka", The transactions of the Institute of Electronics, Information and Communication Engineers A, Dec. 1, 2001, No. 12, pp. 1405 to 1413.

(Continued)

*Primary Examiner* — Brian Casler
*Assistant Examiner* — Joel M Lamprecht
(74) *Attorney, Agent, or Firm* — Antonelli, Terry, Stout & Kraus, LLP.

(57) ABSTRACT

An ultrasound probe includes an ultrasound wave transmit/receive surface coming into contact with a contact surface of a subject, an ultrasound wave transmit/receive section which transmits an ultrasound wave to the subject via the ultrasound wave transmit/receive surface and the contact surface and receives an ultrasound wave reflected in the subject, and a pressing mechanism for performing a pressing operation for applying a pressure to the contact surface perpendicularly to the ultrasound wave transmit/receive surface via the ultrasound wave transmit/receive surface.

22 Claims, 26 Drawing Sheets

U.S. PATENT DOCUMENTS

| | | | |
|---|---|---|---|
| RE34,663 E * | 7/1994 | Seale | 600/587 |
| 5,471,988 A | 12/1995 | Fujio | |
| 5,752,577 A * | 5/1998 | Urakami | 180/164 |
| 5,762,066 A * | 6/1998 | Law et al. | 600/439 |
| 5,860,934 A * | 1/1999 | Sarvazyan | 600/587 |
| 6,004,273 A * | 12/1999 | Sakamoto et al. | 600/459 |
| 6,126,607 A * | 10/2000 | Whitmore et al. | 600/459 |
| 6,296,619 B1 * | 10/2001 | Brisken et al. | 604/22 |
| 6,511,427 B1 | 1/2003 | Sliwa, Jr. | |
| 2002/0068870 A1 | 6/2002 | Alam | |

FOREIGN PATENT DOCUMENTS

| | | |
|---|---|---|
| JP | 05317313 | 12/1993 |
| JP | 11-104131 | 4/1999 |
| JP | 2000-014671 | 1/2000 |
| JP | 2000-060853 | 2/2000 |
| JP | 2000-229078 | 8/2000 |
| JP | 2001-292995 | 10/2001 |
| JP | 2001-519674 | 10/2001 |
| WO | WO 92/21023 | 11/1992 |

OTHER PUBLICATIONS

Takeshi Shiina et al., "Fukugo Jiko Sokanho ni yoru Jitsujikan Tissue Elasticity Imaging", Journal of Medical Ultrasonic, Feb. 15, 1999, vol. 26, No. 2, pp. 57 to 66.

* cited by examiner

FIG. 20

Measurement result frame data $X_{i,j}$
($i=1,2,3,\cdots N$, $j=1,2,3,\cdots M$)

FIG. 21

Measurement quality frame data $Y_{i,j}$
($i=1,2,3,\cdots N$, $j=1,2,3,\cdots M$)

FIG. 23

Decision result frame data $Z_{i,j}$
($i=1,2,3,\cdots N$, $j=1,2,3,\cdots M$)

| | | | | | | | | |
|---|---|---|---|---|---|---|---|---|
| $Z_{1,1}$ | $Z_{2,1}$ | $Z_{3,1}$ | $Z_{4,1}$ | $Z_{5,1}$ | $Z_{6,1}$ | $\cdots$ | $Z_{N,1}$ |
| $Z_{1,2}$ | $Z_{2,2}$ | $Z_{3,2}$ | $Z_{4,2}$ | $Z_{5,2}$ | $Z_{6,2}$ | $\cdots$ | $Z_{N,2}$ |
| $Z_{1,3}$ | $Z_{2,3}$ | $Z_{3,3}$ | $Z_{4,3}$ | $Z_{5,3}$ | $Z_{6,3}$ | $\cdots$ | $Z_{N,3}$ |
| $Z_{1,4}$ | $Z_{2,4}$ | $Z_{3,4}$ | $Z_{4,4}$ | $Z_{5,4}$ | $Z_{6,4}$ | $\cdots$ | $Z_{N,4}$ |
| $Z_{1,5}$ | $Z_{2,5}$ | $Z_{3,5}$ | $Z_{4,5}$ | $Z_{5,5}$ | $Z_{6,5}$ | $\cdots$ | $Z_{N,5}$ |
| $Z_{1,6}$ | $Z_{2,6}$ | $Z_{3,6}$ | $Z_{4,6}$ | $Z_{5,6}$ | $Z_{6,6}$ | $\cdots$ | $Z_{N,6}$ |
| $Z_{1,7}$ | $Z_{2,7}$ | $Z_{3,7}$ | $Z_{4,7}$ | $Z_{5,7}$ | $Z_{6,7}$ | $\cdots$ | $Z_{N,7}$ |
| $\vdots$ | $\vdots$ | $\vdots$ | $\vdots$ | $\vdots$ | $\vdots$ | $\ddots$ | $\vdots$ |
| $Z_{1,M}$ | $Z_{2,M}$ | $Z_{3,M}$ | $Z_{4,M}$ | $Z_{5,M}$ | $Z_{6,M}$ | $\cdots$ | $Z_{N,M}$ |

Image vertical axis direction → ; Image horizontal axis direction ↑

FIG. 24

Decision result frame data $Z_{i,j}$
Example of ($i=1,2,3,\cdots N$, $j=1,2,3,\cdots M$)

| | | | | | | | | |
|---|---|---|---|---|---|---|---|---|
| 1 | 1 | 1 | 1 | 1 | 1 | 1 | $\cdots$ | 1 |
| 1 | 1 | 1 | 1 | 1 | 1 | 1 | $\cdots$ | 1 |
| 1 | 1 | 0 | 0 | 1 | 1 | 1 | $\cdots$ | 1 |
| 1 | 1 | 0 | 0 | 0 | 1 | 1 | $\cdots$ | 1 |
| 1 | 0 | 0 | 0 | 0 | 0 | 1 | $\cdots$ | 1 |
| $\vdots$ | $\vdots$ | $\vdots$ | $\vdots$ | $\vdots$ | $\vdots$ | $\vdots$ | $\ddots$ | $\vdots$ |
| 1 | 1 | 1 | 1 | 1 | 1 | 1 | $\cdots$ | 1 |

Image vertical axis direction → ; Image horizontal axis direction ↑

ULTRASONIC PROBE AND ULTRASONIC ELASTICITY IMAGING DEVICE

TECHNICAL FIELD

The present invention relates to an ultrasound imaging apparatus and an ultrasound probe of the apparatus, by which a tomographic image of a target part in a subject is obtained by using ultrasound waves, and particularly relates to an ultrasound elasticity imaging apparatus and an ultrasound probe of the apparatus, by which a distortion and a modulus of elasticity are calculated for each point in a subject based on ultrasound received signal data of consecutive time-series frames to display an elastic image indicating the hardness of a tissue.

BACKGROUND ART

For ultrasound imaging apparatuses, the following methods are available: one method is to apply an external force to a subject via an ultrasound wave transmit/receive surface of an ultrasound probe, determine a displacement of each point in the subject by using a correlation operation of ultrasound wave received signal data on a pair of adjacent time-series frames, measure a distortion by performing spatial differentiation on the displacement, and form an image of distortion data, and another method is to form an image of elastic modulus data such as a Young's modulus of a tissue from a stress distribution caused by an external force and distortion data (e.g., Japanese Patent Application Laid-Open No. 5-317313 and Japanese Patent Application Laid-Open No. 2000-60853). The external force applied to the subject includes pressing and depressing the subject. Hereinafter, the external force will be simply referred to as "pressing" Ultrasound received signal frame data at a given time reflects, as information, the configuration and arrangement of tissues in the subject at that time. In a method for obtaining tissue elasticity information by using ultrasound waves, first by using ultrasound received signal data of a pair of frames obtained at regular time intervals, a displacement of each part of a tissue is calculated. The displacement is caused by a pressure applied between the regular time intervals. Then, displacement information undergoes spatial differentiation, so that distortions are calculated for all points in a region of interest (ROI) and an elastic image is constructed and displayed. With an elastic image obtained based on such distortion/elasticity modulus data (hereinafter, referred to as elastic frame data), the hardness of a tissue can be measured and displayed.

In order to obtain high-quality elastic image data, it is preferable to apply a pressure causing a tissue of interest to have a distortion of about 0.5% to 1%. In a time phase when a distortion within a proper range is not applied, extracted elastic image data is disturbed. When obtaining ultrasound received signal frame data of a pair of frames at regular time intervals, a high pressing speed at a certain time causes large distortion of a tissue at that time, and a low pressing speed at a certain time causes small distortion of a tissue at that time. Therefore, the quality of two or more elastic image data (particularly distortion image data) obtained in a series of pressing processes depends upon a pressing speed at a time when obtaining ultrasound received signal frame data of a pair of frames for constituting the elastic image data.

In elasticity imaging using a conventional ultrasound imaging apparatus, a tissue of interest is manually pressed by an ultrasound probe. Thus, it is difficult to keep pressing within a pressing speed range suitable for high image quality all the time in a series of pressing processes. Further, a pressing speed is not constant at respective times, so that a plurality of outputted elastic image data becomes temporally discontinuous and elastic images become discontinuous between frames. Further, it is not possible to avoid a movement of hands in the pressing process. A pressing direction varied between times also causes discontinuity of the elastic image data having been sequentially obtained. Therefore, the quality of an elastic image depends upon the technique of the operator.

At the time intervals for obtaining ultrasound received signal frame data, a tissue of interest is moved out of a measuring cross section by a pressure in the short axis direction of the probe, or displaced at high speed in the long axis direction or pressing direction of the probe, so that the tissue of interest may deviate from ROI set by the imaging apparatus. In this manner, due to an improper pressing direction or an excessive speed, ROI set by the imaging apparatus may have an error (correlation operation error) region, in which a correct displacement cannot be calculated. In a deep region where transmitted ultrasound waves can not reach due to attenuation and in a region with few ultrasound reflectors (a cyst and a lesion having a liquid therein), ROI set by the imaging apparatus may have an error (correlation operation error) region, in which a correct displacement cannot be calculated, because no received signal reflecting a property of the tissue of interest with sufficient intensity cannot be obtained. Moreover, ROI set by the imaging apparatus may include an error region where the calculation of a displacement is insignificant, due to the shape of the ultrasound probe and the pattern of a tissue of interest, for example, in a region where the ultrasound probe is not in contact with the subject. In these cases, a distortion image is not correctly displayed in the error region.

Furthermore, a region having a displacement close to 0 may be entirely distributed in ROI set by the imaging apparatus due to a pressing speed of 0 or an insufficient pressing speed. Such pressing speeds occur when a pressure is not applied to a tissue of interest at time intervals for obtaining a pair of ultrasound received signal frame data and a pressing speed on a tissue of interest is too low. In this case, a distortion image indicating distortions calculated using the displacement has a low contrast over the ROI.

In elastic imaging using the conventional ultrasound imaging apparatus, an image is constructed and displayed for all the measuring points of the set ROI without evaluating whether data (distortion or modulus of elasticity) outputted as an arithmetic result is worth displaying or not (reliability and quality of data). Therefore, even though image information on a region calculated under improper conditions is not worth displaying, the image information cannot be discriminated from information worth displaying. As a result, an elastic image of one frame is constructed such that a region worth displaying and a region not worth displaying are mixed, reducing the reliability of an elastic image.

In the conventional ultrasound imaging apparatus, whether a pressing operation for applying an external force from a body surface to a living tissue of the subject is proper or not is not considered. Hence, it is not always possible to obtain a proper elastic image.

In other words, an elastic image is obtained by determining a modulus of elasticity from a displacement (distortion) of each part of a living tissue and a pressure or the like, and imaging a distortion pattern qualitatively or a modulus of elasticity quantitatively based on frame data of two tomographic images different in time series. The tomographic images have been obtained by applying an external force to a living tissue. A distortion of each part of a living tissue varies according to a pressing operation including a pressure, a pressing speed, a pressing time, a pressing direction and the like. Without a certain distortion difference between adjacent two frames, a proper elastic image cannot be generated.

Particularly, for simplicity, an external force is applied by pressing the ultrasound probe to a body surface of the subject in many cases, though an external force may be applied by mechanical device. A pressing state is considerably changed by the feeling of the operator, and thus it is not always possible to obtain a proper elastic image. Similarly, because of variations among subjects, even when an operation is performed in a uniform pressing state, a proper elastic image cannot be always obtained.

Further, a pressing direction and the way to press may cause lateral displacement on a living tissue. Also in this pressing operation, an elastic image may include disturbance (noise) caused by lateral displacement and a proper elastic image may not be obtained.

The present invention is devised in view of these circumstances. An object of the present invention is to provide an ultrasound imaging apparatus which can stably form a high-quality elastic image in a given time phase during elastic imaging. An object of the present invention is also to provide an ultrasound imaging apparatus, by which when typical and ideal data is hard to obtain in elastic imaging, a region of image information including an elastic value not worth displaying is recognized as, e.g., noise, and an elastic image reflecting the information is constructed, high-quality elastic imaging is enabled. Moreover, an object of the present invention is to provide the operator with pressing operation information for obtaining a proper elastic image.

DISCLOSURE OF THE INVENTION

In order to attain the object, the present invention relates to an ultrasound probe comprising an ultrasound wave transmit/receive surface coming into contact with the contact surface of a subject, an ultrasound wave transmit/receive section which transmits an ultrasound wave to the subject via the ultrasound wave transmit/receive surface and the contact surface and receives an ultrasound wave reflected in the subject, and a pressing mechanism for performing a pressing operation for applying a pressure to the contact surface perpendicularly to the ultrasound wave transmit/receive surface via the ultrasound wave transmit/receive surface.

The pressing mechanism preferably comprises a holding part held by an operator, and an actuator for performing the pressing operation by changing a distance between the ultrasound wave transmit/receive surface and the holding part.

The actuator preferably comprises a rack connected to one of the ultrasound wave transmit/receive surface and the holding part, a pinion which is connected to the other of the ultrasound wave transmit/receive surface and the holding part and engages with the rack, and a motor for driving the pinion.

The actuator preferably comprises a cylinder connected to one of the ultrasound wave transmit/receive surface and the holding part, a piston which is connected to the other of the ultrasound wave transmit/receive surface and the holding part and inserted into the cylinder, and a pump for feeding liquid to the cylinder.

It is preferable that the contact surface is disposed in the subject, the ultrasound wave transmit/receive surface is inserted into the subject, and the pressing mechanism performs the pressing operation in the subject.

The pressing mechanism preferably comprises a support surface coming into contact with an opposed contact surface of the subject, the opposed contact surface being opposed to the contract surface in the subject, and an actuator for performing the pressing operation by changing a distance between the ultrasound wave transmit/receive surface and the support surface.

The actuator preferably comprises a rack connected to one of the ultrasound wave transmit/receive surface and the support surface, a pinion which is connected to the other of the ultrasound wave transmit/receive surface and the support surface and engages with the rack, and a motor for driving the pinion.

The actuator preferably comprises a bag for supplying liquid between the ultrasound wave transmit/receive surface and a surface of the ultrasound wave transmit/receive section, and a pump for changing an amount of the liquid in the bag, and the ultrasound wave transmit/receive surface includes a surface of the bag.

The bag preferably comprises a first part serving as the ultrasound wave transmit/receive surface and a second part other than the first part. The second part comprises a shell which is lower in flexibility than the first part and regulates the moving direction of the first part.

The actuator preferably comprises a bag for supplying liquid between the ultrasound wave transmit/receive surface and the support surface, and a pump for changing an amount of the liquid in the bag.

The actuator preferably comprises a plurality of bags for supplying liquid between the ultrasound wave transmit/receive surface and the support surface, and a pump for changing an amount of the liquid in each of the plurality of bags. The direction of the pressing operation is selected from a plurality of directions by selectively using at least one of the plurality of bags.

Preferably, the ultrasound probe further comprises a cylindrical casing for storing the ultrasound wave transmit/receive section, and the actuator comprises a ring-like bag which supplies liquid between the ultrasound wave transmit/receive surface and a surface of the ultrasound wave transmit/receive section and is attached around the casing, and a pump for changing an amount of the liquid in the bag. The ultrasound wave transmit/receive surface includes a surface of the bag.

Preferably, the ultrasound probe further comprises a stopper which is attached around the bag and acts as the support surface.

Preferably, the ultrasound probe further comprises a pressure measuring section for measuring a pressure applied to the contact surface, and a pressure control section for controlling the pressing mechanism according to the pressure measured by the pressure measuring section.

Preferably, the pressing mechanism comprises a bag having liquid and performs the pressing operation by changing an amount of the liquid in the bag, and the pressure measuring section measures a pressure applied to the contact surface by measuring a pressure of the liquid in the bag.

Preferably, the ultrasound probe further comprises a first casing for storing the ultrasound wave transmit/receive section and a second casing for storing the pressing mechanism. The first casing comprises a first holding part held by the operator and the second casing comprises a second holding part which is held by the operator and attached relative to the first holding part. The pressing mechanism comprises an actuator for performing the pressing operation by changing a distance between the ultrasound wave transmit/receive surface and the second holding part.

The pressing mechanism preferably comprises a holding part held by the operator and a control switch which is disposed on a position enabling the switch to be operable with a hand of the operator who holds the holding part and controls the pressing operation of the pressing mechanism.

Further, the present invention relates to an ultrasound elasticity imaging apparatus comprising the ultrasound probe, an ultrasound wave transmitting section for outputting an ultrasound signal for driving the ultrasound probe, a displacement measuring section which obtains two tomographic image data different in time series from a reflected echo signal received from the ultrasound probe and measures a displacement of each part in the subject based on the two tomographic image data, an elasticity modulus calculating section for calculating a modulus of elasticity of a tissue of each part in the subject based on displacement data of each part in the subject, the displacement data being measured by the displacement measuring section, an image generating section for generating an elastic image based on a modulus of elasticity determined by the elasticity modulus calculating section, and a display section for displaying the generated elastic image.

Preferably, the ultrasound elasticity imaging apparatus further comprises a pressing period control section for controlling a pressing period of the pressing mechanism according to a time interval of the two tomographic image data.

Moreover, the present invention relates to an ultrasound elasticity imaging apparatus comprising a signal processing section for processing a signal detected by an ultrasound probe coming into contact with a subject tissue to generate a tomographic image and a distortion elastic image, a display value evaluating section for evaluating the display value of the generated distortion elastic image based on various data used in a process of generating the distortion elastic image, an information adding section for adding hue information or monochrome information to the distortion elastic image according to the evaluation result of the display value evaluating section, and a display section for displaying the tomographic image and the distortion elastic image including information added by the information adding section.

Further, the present invention relates to an ultrasound elasticity imaging apparatus comprising an ultrasound wave transmit/receive section which transmits and receives an ultrasound wave to and from a subject and outputs a reflected echo signal, a tomographic scanning section for repeatedly obtaining ultrasound received signal frame data in the subject including a kinetic tissue, with an ultrasound cycle by using a reflected echo signal from the ultrasound wave transmit/receive section, a signal processing section for performing predetermined signal processing on the time-series ultrasound received signal frame data obtained by the tomographic scanning section, a monochrome data converting section for converting time-series tomographic frame data from the signal processing section to monochrome tomographic image data, a displacement measuring section for generating, based on the time-series ultrasound received signal frame data obtained by the tomographic scanning section, displacement frame data indicating a movement or displacement of each point on the tomographic image, a pressure measuring section for measuring or estimating a pressure in a body cavity of a diagnosed part of the subject to generate pressure data, a distortion/elasticity modulus calculating section for generating elastic frame data indicating a distortion and a modulus of elasticity of each point on the tomographic image based on the displacement frame data and the pressure data, a display value evaluating section for devaluating the display value of the elastic frame data based on various data used in a process of generating the elastic frame data, an information adding section for adding hue information or monochrome brightness information to the elastic frame data according to an evaluation result of the display value evaluating section, and a display section for displaying the monochrome elastic image data and the elastic frame data including information added by the information adding section.

The information adding section preferably constructs elastic frame data by adding image information with a gradation to a region worth displaying and adding single image information to a region not worth displaying, the single information being different from the image information added with the gradation to the region worth displaying, so that both of the region are distinguishable on an image.

The information adding section preferably constructs elastic frame data by adding image information with a gradation to a frame worth displaying and adding single image information to a frame not worth displaying, the single information being different from the image information added with the gradation to the region worth displaying, so that both of the region are distinguishable on an image.

The display value evaluating section performs statistical processing using, as a population, the element data of various data used for the process of generating the elastic frame data, and evaluates the display value of the elastic frame data based on a statistical characteristic.

The display value evaluating section preferably evaluates the display value of the elastic frame data based on the displacement frame data outputted from the displacement measuring section.

The display value evaluating section preferably evaluates the display value of the elastic frame data based on the pressure data outputted from the pressure measuring section.

The display value evaluating section preferably evaluates the display value of the elastic frame data based on the elastic frame data outputted from the distortion/elasticity modulus calculating section.

Preferably, the display value evaluating section automatically sets at least one of the position and range of a region of interest for displaying the elastic frame data, according to a display value evaluation result of the elastic frame data.

The display section preferably displays only the monochrome tomographic image data but does not display the elastic frame data according to an evaluation result of the display value evaluating section.

Moreover, the present invention relates to an ultrasound elastic imaging apparatus comprising a signal processing section for processing a signal detected by an ultrasound probe coming into contact with a subject tissue to generate a tomographic image and a distortion elastic image, a display value evaluating section for evaluating the display value of the generated distortion elastic image based on various data used in a process of generating the distortion elastic image, and a display section for displaying only the tomographic image but does not display the distortion elastic image according to an evaluation result of the display value evaluating section.

Further, the present invention relates to an ultrasound elasticity imaging apparatus comprising an ultrasound probe for transmitting and receiving an ultrasound wave to and from a subject, ultrasound wave transmitting device for outputting an ultrasound signal for driving the ultrasound probe, pressing device for applying an external force to the subject, displacement measuring device which obtains two tomographic image data different in time series from a reflected echo signal received from the ultrasound probe and measures a displacement of each part based on the two tomographic image data, an elasticity modulus calculating section for calculating a modulus of elasticity of a tissue of each part based on displacement data of each part of the subject, the displacement data being measured by the displacement measuring device, image generating device for generating an elastic image based on a modulus of elasticity determined by the elasticity modulus calculating device, and display device for displaying the generated elastic image, wherein the device further comprises pressing decision device for analyzing the displacement data to decide whether a pressing operation of the pressing device is proper or not, and decision output device for displaying a decision result of the pressing decision device on the display device.

As described above, whether a pressing operation is proper or not is immediately displayed on the display device, and thus the operator can obtain a proper elastic image by adjusting a pressure operation with pressing device (e.g., probe) depending upon whether a displayed pressing state is proper or not. Further, whether a pressing operation is proper or not is decided by analyzing displacement data, and thus it is possible to decide the suitability of a pressing operation in consideration of variations among subjects. Consequently, it is possible to achieve elasticity imaging with excellent usability for the operator.

In this case, the pressing decision device determines a distortion factor distribution in the tomographic image based on displacement data, and decides whether a pressing operation performed by the pressing device is proper or not depending upon whether the distortion factor distribution is within a proper range or not. Additionally or instead of this operation, the pressing decision device can determine a degree of lateral displacement in a tomographic image based on displacement data, and decide whether a pressing operation performed by the pressing device is proper or not depending upon whether the degree of lateral displacement is within a proper range or not. Moreover, the decision output device outputs, through display or/and sound, a guidance for correcting a pressing operation based on a decision result.

BRIEF DESCRIPTION OF THE DRAWINGS

FIG. 20 is a diagram showing an example of measurement result frame data stored in a frame memory circuit of FIG. 19;

FIG. 21 is a diagram showing an example of measurement quality frame data constructed by a measurement quality evaluating circuit of FIG. 19;

FIG. 23 is a diagram showing an example of decision result frame data constructed by a display decision circuit of FIG. 22;

FIG. 24 is a diagram showing an example of specific numeric values of the decision result frame data shown in FIG. 23;

BEST MODE FOR CARRYING OUT THE INVENTION

Figure 1:
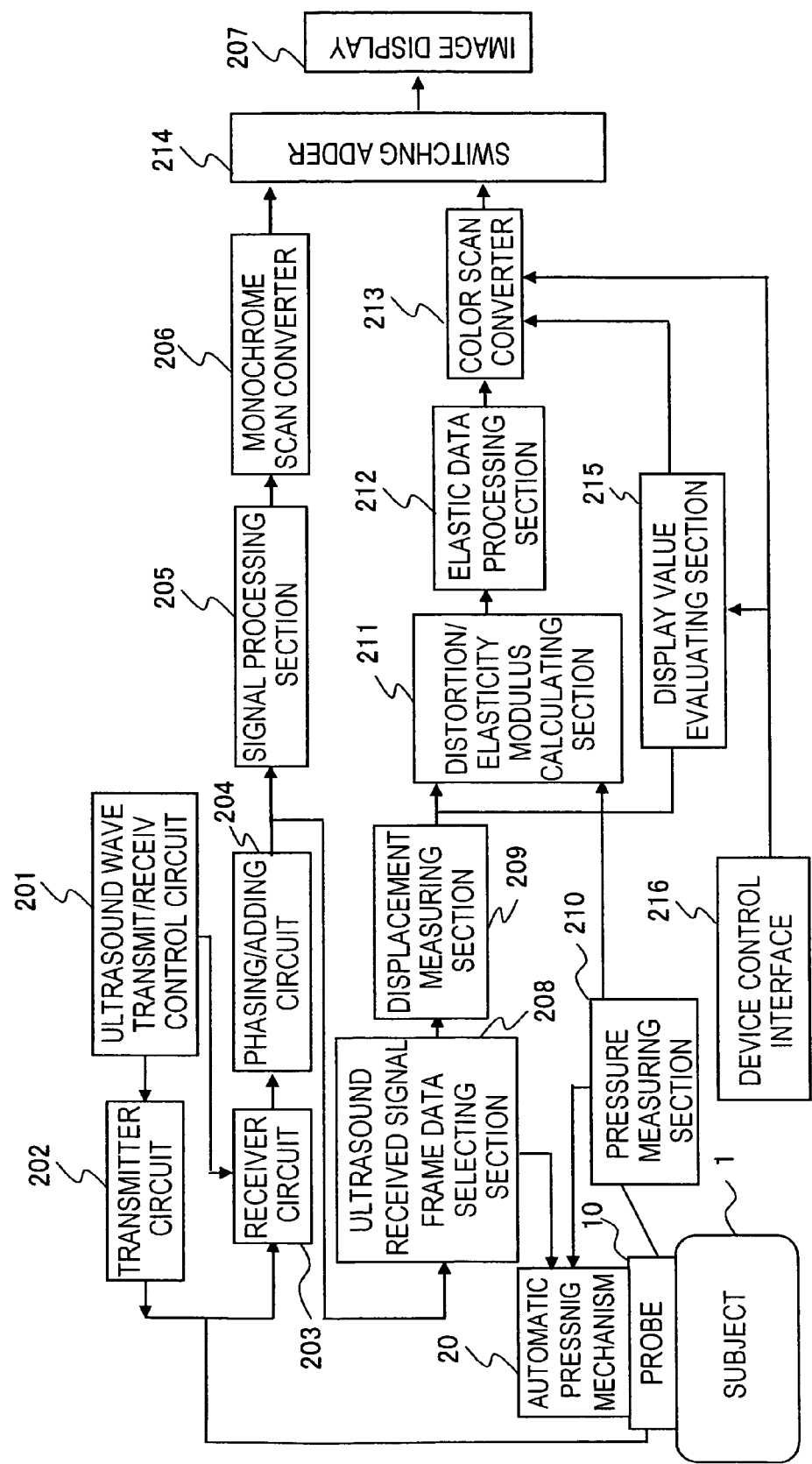
FIG. 1 is a block diagram showing the configuration of an embodiment of an ultrasound imaging apparatus according to the present invention.

The following will specifically describe examples of the present invention in accordance with the accompanying drawings. FIG. 1 is a block diagram showing an embodiment of an ultrasound imaging apparatus according to the present invention. The ultrasound imaging apparatus obtains a tomographic image of a target part in a subject 1 by using ultrasound waves and displays an elastic image indicating the hardness of a living tissue. As shown in FIG. 1, the ultrasound imaging apparatus comprises an ultrasound probe 10 having an automatic pressing mechanism 20, an ultrasound wave transmit/receive control circuit 201, a transmitter circuit 202, a receiver circuit 203, a phasing/adding circuit 204, a signal processing section 205, a monochrome scan converter 206, an image display 207, an ultrasound received signal frame data selecting section 208, a displacement measuring section 209, a pressure measuring section 210, a distortion/elasticity modulus calculating section 211, an elastic data processing section 212, a color scan converter 213, a switching adder 214, a display value evaluating section 215, and a device control interface 216.

The ultrasound probe 10 is formed of a number of oscillators arranged like strips. The ultrasound probe 10 mechanically or electronically performs beam scanning, transmits ultrasound waves to the subject 1, and receives ultrasound waves reflected in the subject 1. The ultrasound wave transmit/receive control circuit 201 controls time to transmit and receive ultrasound waves. The transmitter circuit 202 drives the ultrasound probe 10 to generate a transmission pulse for generating ultrasound waves, and sets, at a certain depth, a convergent point of ultrasound waves transmitted by a transmission phasing/adding circuit included in the transmitter circuit 202. The receiver circuit 203 amplifies a reflected echo signal, which has been received by the ultrasound probe 10, with a predetermined gain. The number of amplified received signals corresponding to the number of oscillators are inputted as separate received signals to the phasing/adding circuit 204. The phasing/adding circuit 204 is fed with the received signals having been amplified by the receiver circuit 203, controls the phases of the signals, and forms ultrasound beams for one or more convergent points. The signal processing section 205 is fed with the received signals from the phasing/adding circuit 204 and performs kinds of signal processing including gain correction, log compression, detection, edge enhancement, filter processing and the like.

The ultrasound probe 10, the ultrasound wave transmit/receive control circuit 201, the transmitter circuit 202, the receiver circuit 203, the phasing/adding circuit 204, and the signal processing section 205 constitute ultrasound wave transmit/receive device. A tomographic image is obtained by using the ultrasound probe 10 to scan the inside of the subject 1 with an ultrasound beam in a fixed direction.

The monochrome scan converter 206 comprises tomographic scanning device for obtaining ultrasound received signal frame data of the subject 1, which includes a kinetic tissue, with an ultrasound cycle by using a reflected echo signal outputted from the signal processing section 205 of the ultrasound wave transmit/receive device and reading the ultrasound received signal frame data with a cycle of a television system to display the data, and device for controlling the system, for example, the monochrome scan converter 206 comprises an AD converter for converting a reflected echo signal from the signal processing section 205 to a digital signal, two or more pieces of frame memory for storing tomographic image data, which has been digitized by the AD converter, in time series, and a controller for controlling the operations thereof.

The image display 207 displays time-series tomographic image data obtained by the monochrome scan converter 206, that is, a B-mode tomographic image, and comprises a DA converter for converting, to an analog signal, image data outputted from the monochrome scan converter 206 through the switching adder 214, and a color monitor which is fed with an analog video signal from the DA converter and displays the signal as an image.

In the present embodiment, the ultrasound received signal frame data selecting section 208 and the displacement measuring section 209 branch off from the output of the phasing/adding circuit 204, the pressure measuring section 210 is provided in parallel with these sections, the distortion/elasticity modulus calculating section 211 is provided in the subsequent stage of the pressure measuring section 210 and the displacement measuring section 209, the display value evaluating section 215 branches off from the output of the displacement measuring section 209, the elastic data processing section 212 and the color scan converter 213 are provided in the subsequent stage of the distortion/elasticity modulus calculating section 211, and the switching adder 214 is provided on the output of the monochrome scan converter 206 and the color scan converter 213. The display value evaluating section 215 and the color scan converter 213 can be freely controlled by an operator or the like through the device control interface 216.

The ultrasound received signal frame data selecting section 208 sequentially obtains, in frame memory included in the ultrasound received signal frame data selecting section 208, ultrasound received signal frame data sequentially outputted in time series from the phasing/adding circuit 204 with a frame rate of the ultrasound imaging apparatus (the obtained ultrasound received signal frame data will be referred to as ultrasound received signal frame data N), selects one of past ultrasound received signal frame data N-1, N-2, N-3, ..., N-M according to a control command of the ultrasound imaging apparatus (the selected frame data will be referred to as ultrasound received signal frame data X), and outputs a pair of ultrasound received signal frame data N and ultrasound received signal frame data X to the displacement measuring section 209. A signal outputted from the phasing/adding circuit 204 is not limited to the ultrasound received signal frame data. For example, I and Q signals obtained by complex-demodulating an ultrasound received signal may be used.

The ultrasound received signal frame data selecting section 208 obtains period information between the selected pair of ultrasound received signal frame data N and X, and the pressing operation of the automatic pressing mechanism 20 is controlled according to the period. The following will describe an example of the operations.

A period between the pair of ultrasound received signal frame data N and X selected by the ultrasound received signal frame data selecting section 208 is determined according to the period of ultrasound received signal frame data which is outputted from the phasing/adding circuit 204 and inputted to the ultrasound received signal frame data selecting section 208 and the number of ultrasound received signal frame data thinned out between the past ultrasound received signal frame data X and the current ultrasound received signal frame data N, which constitute the pair of ultrasound received signal frame data. For example, when ultrasound received signal frame data serving as the output of the phasing/adding circuit 204 has a period of 40 frames per second and a period between the pair of ultrasound received signal frame data becomes 20 frames per second when the number of frames thinned out between the pair of ultrasound received signal frame data N and X is one. The automatic pressing mechanism 20 obtains period information between the pair of ultrasound received signal frame data N and X and controls the pressing speed of a pressing operation based on the obtained period information.

For example, under the above conditions, when the period of ultrasound received signal frame data serving as output from the phasing/adding circuit 204 is 40 frames per second and a period between the pair of ultrasound received signal frame data N and X is 20 frames per second, it is assumed that a pressure is continuously applied at a pressing speed V0 enabling a distortion of 0.7% which is suitable for high image quality of a tissue of interest. Under these circumstances, when the period of ultrasound received signal frame data serving as output from the phasing/adding circuit 204 is changed to 20 frames per second by a change of the imaging conditions of the ultrasound imaging apparatus, the period between the pair of ultrasound received signal frame data N and X is reduced by half to 10 frames per second. In this case, when a pressure is still applied at the pressing speed V0, intermittence time between the ultrasound received signal frame data is doubled, and thus a distortion of the tissue of interest increases to 1.4%, which deviates from a range of distortions suitable for high image quality. As a result, continuously outputted elastic image data is disturbed. Hence, in the automatic pressing mechanism 20 of the present embodiment, period information on ultrasound received signal frame data is obtained. For example, under the above circumstances, the pressing speed is reduced by half to V0/2. Hence, even when an ultrasound wave transmit/receive period varies due to a change of the imaging conditions of the ultrasound imaging apparatus, it is possible to automatically control a pressing operation so as to have the optimum pressing speed for obtaining a high-quality elastic image.

The automatic pressing mechanism 20 can arbitrarily switch a pressing speed, an amount of compression (amplitude) accumulated in continuous pressurization/decompression, and the setting of a pressing operation. The setting includes a pressure threshold value for stopping the pressing operation.

The displacement measuring section 209 performs one-dimensional or two-dimensional correlation processing based on the pair of ultrasound received signal frame data selected by the ultrasound received signal frame data selecting section 208, measures a displacement or a movement vector (direction and size of a displacement) of each measuring point on a tomographic image, and generates displacement frame data. A method of detecting a movement vector includes a block matching method and a gradient method which are disclosed in Japanese Patent Application Laid-Open No. 5-317313. In the block matching method, an image is divided into, e.g., blocks of N×N pixels, the previous frame is searched for a block most approximate to a block of interest in the current frame, and predictive coding is performed with reference to the block.

The pressure measuring section 210 measures or estimates a pressure applied to a target part of the subject 1. The pressure measuring section 210 measures a pressure applied between the subject 1 and the probe head of the ultrasound probe 10. For example, the pressure measuring section 210 can be configured as follows: a pressure sensor for detecting a pressure applied to a rod-like member is attached to a side of the probe head, a pressure between the probe head and the subject 1 is measured in a given time phase, and a measured pressure is transmitted to the distortion/elasticity modulus calculating section 211. The kind of the pressure sensor is not particularly limited. For example, capacitance pressure sensors and wire resistance pressure sensors are available.

The distortion/elasticity modulus calculating section 211 calculates a distortion and a modulus of elasticity of each measuring point on a tomographic image based on displacement frame data (movement amount) and a pressure which are outputted from the displacement measuring section 209 and the pressure measuring section 210, generates numeric data (elastic frame data) of a distortion or a modulus of elasticity, and outputs the data to the elastic data processing section 212. For example, in the arithmetic operation of a distortion in the distortion/elasticity modulus calculating section 211, pressure data is not necessary. A distortion is calculated by performing spatial differentiation on a displacement. For example, a Young's modulus Ym, one of moduli of elasticity, is determined by dividing a stress (pressure) on each arithmetic point by a distortion on each arithmetic point as expressed in the formula below:

$$Ym_{i,j} = \text{pressure (stress)}_{i,j} / (\text{distortion}_{i,j})$$

$(i, j = 1, 2, 3, \ldots)$ where indexes i and j represent the coordinates of frame data.

The elastic data processing section 212 performs various kinds of image processing such as smoothing performed on elastic frame data from the distortion/elasticity modulus calculating section 211 in a coordinate plane, contrast optimization, and smoothing in the time-axis direction between the frames, and outputs processed elastic frame data to the color scan converter 213.

The color scan converter 213 comprises hue information converting device which is fed with elastic frame data outputted from the elastic data processing section 212 and a command from the device control interface 216 or an upper limit value and a lower limit value of a gradation selection range in elastic frame data outputted from the elastic data processing section 212, and adds, as elastic image data, hue information including red, green, and blue from the elastic frame data. For example, regarding a region measured with a large distortion in elastic frame data outputted from the elastic data processing section 212, the hue information converting device converts the corresponding region in the elastic image data to a red code. Regarding a region with a small distortion, the hue information converting device converts the corresponding region in the elastic image data to a blue code. The color scan converter 213 may be a monochrome scan converter. Regarding the region measured with a large distortion, the corresponding region in the elastic image data may be increased in brightness. Regarding the region measured with a small distortion, the corresponding region in the elastic image data may be reduced in brightness.

The switching adder 214 is fed with monochrome tomographic image data from the monochrome scan converter 206 and color elastic image data from the color scan converter 213, adds or switches images, and outputs only one of the monochrome tomographic image data and the color elastic image data or both of the image data after addition/combination. For example, as described in Japanese Patent Application Laid-Open No. 2000-60853, a monochrome tomographic image and a color or monochrome elastic image obtained by the monochrome scan converter may be simultaneously displayed on two screens. Further, for example, a color elastic image may be translucently superimposed and displayed on a monochrome tomographic image. Image data outputted from the switching adder 214 is outputted to the image display 207.

Figure 2:
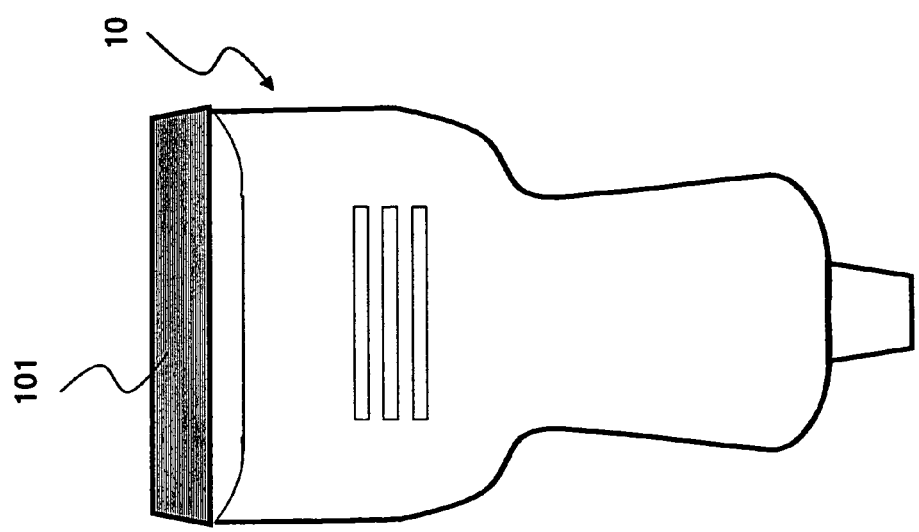
FIG. 2 is an outside drawing showing a liner array ultrasound probe.

FIG. 2 is a diagram showing the appearance of an ordinary one-dimensional linear array ultrasound probe. Elements of oscillators which generate ultrasound waves and receive reflected echo are arranged in alignment on an ultrasound wave transmit/receive surface 101 of the ultrasound probe 10. The oscillators generally have the function of transforming an inputted pulse wave or a transmitted signal of a continuous wave into an ultrasound wave and transmitting the ultrasound wave, and the function of receiving an ultrasound wave reflected from the inside of the subject 1, transforming the ultrasound wave into a received signal, which is an electric signal, and outputting the signal.

Figure 3:
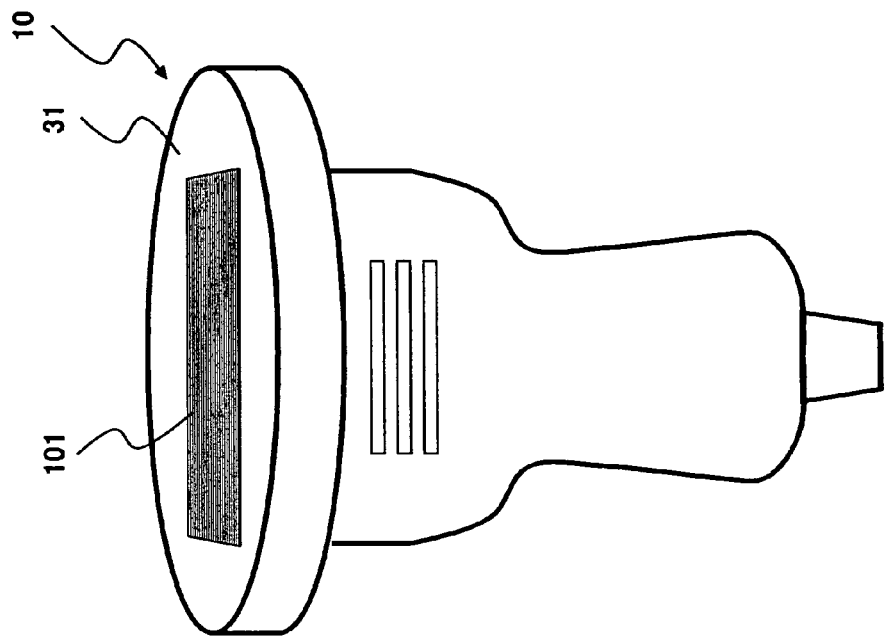
FIG. 3 is an outside drawing showing an ultrasound probe having a pressing plate.

FIG. 3 is an outside drawing of the ultrasound probe 10 for obtaining an elastic image with ultrasound waves. The ultrasound probe 10 comprises a pressing plate 31 flush with the ultrasound wave transmit/receive surface 101. When obtaining an elastic image, while transmitting and receiving ultrasound waves through the ultrasound wave transmit/receive surface 101, a pressing surface constituted of the ultrasound wave transmit/receive surface 101 and the pressing plate 31 is brought into contact with the subject 1 and the subject 1 is pressed by moving the pressing surface up and down to provide a target part of the subject 1 with a stress distribution. The pressing surface may be manually moved up and down by the operator or the automatic pressing mechanism 20 described below.

Figure 4:
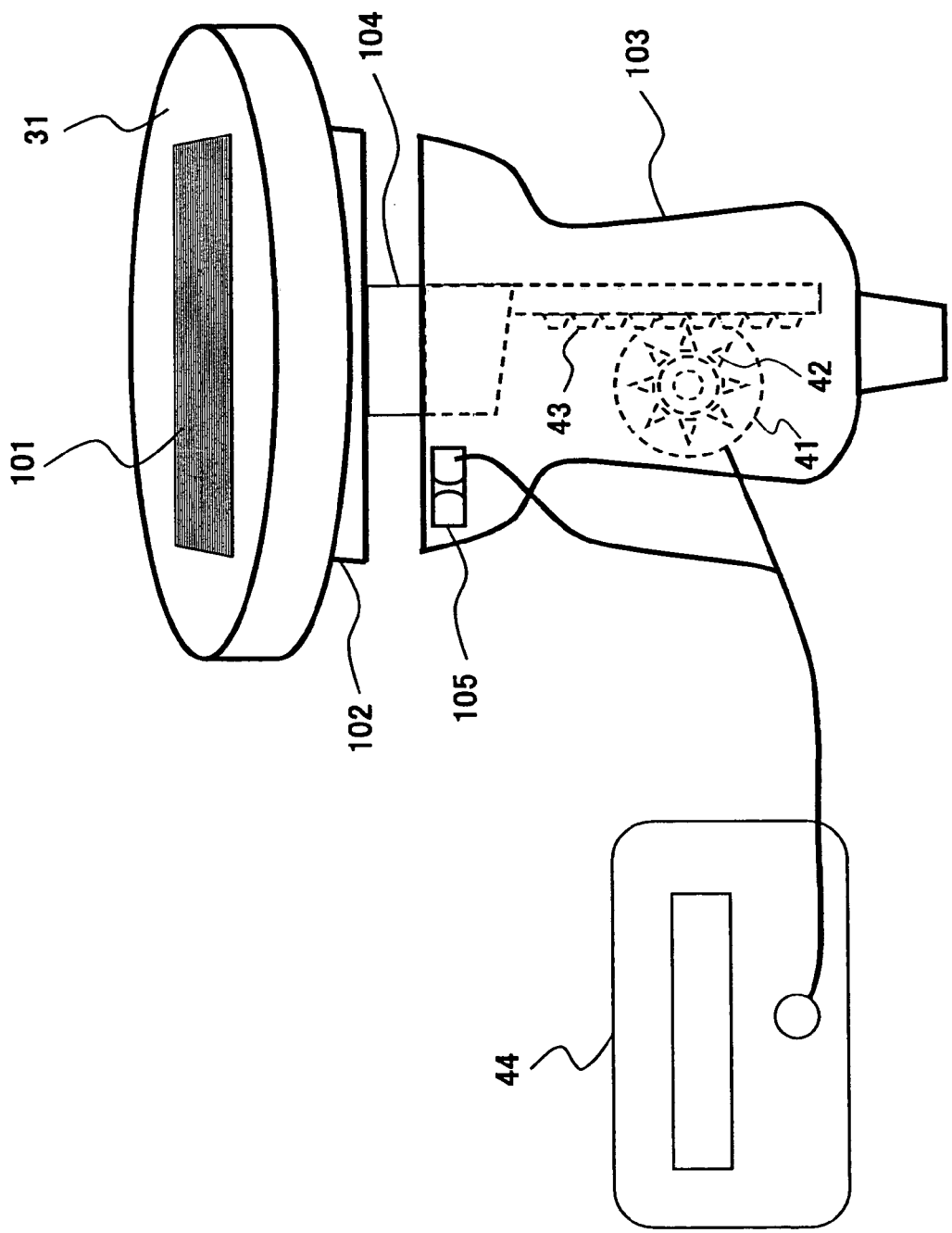
FIG. 4 is a diagram showing an ultrasound probe including an automatic pressing mechanism of a motor mechanism.

As an embodiment of the automatic pressing mechanism 20 for performing the pressing operation of the ultrasound probe, FIG. 4 shows an example using driving force of an actuator including a motor mechanism. In FIG. 4, the automatic pressing mechanism 20 moves up and down a pressing stage 102, on which the pressing surface constituted of the ultrasound wave transmit/receive surface 101 and the pressing plate 31 is separated. The automatic pressing mechanism 20 is constituted of a rack and pinion. The rack and pinion have a pinion 42 on the rotating shaft of a motor mechanism 41 which is stored in a probe holding part 103 of the ultrasound probe 10 held by the operator, and a rack 43 on a support member 104 of the pressing stage 102. The motor mechanism 41 moves up and down the pressing stage 102 relative to the probe holding part 103 through the rack and pinion in response to a control command from an external motor control section 44. In other words, when the operator holds the probe holding part 103 to bring the pressing stage 102 into contact with the subject 1, an actuator changes a distance between the pressing stage 102 and the probe holding part 103, so that a pressure is applied to the subject 1 through the pressing stage 102. A switch 105 is an interface which allows the operator to operate the automatic pressing mechanism 20 (motor control section 44), and the switch 105 is disposed on a position where the switch 105 is operable with fingers of the operator who holds the probe holding part 103. The operator can adjust the turning on/off of the automatic pressing mechanism 20, a working pressure, and a working period through the switch 105. The motor mechanism 41 may be a mechanism using an electromagnetic motor, an ultrasound motor, and so on. A mechanism for transmitting power from the motor mechanism 41 to the pressing stage 102 is not limited to the rack and pinion. For example, a cam may be provided in the motor mechanism 41 to vertically drive the support member 104 according to the shape of the cam. Instead of a power transmission mechanism such as a rack and pinion, a direct-acting motor or the like may be directly connected to the pressing stage 102 and driven.

Figure 5:
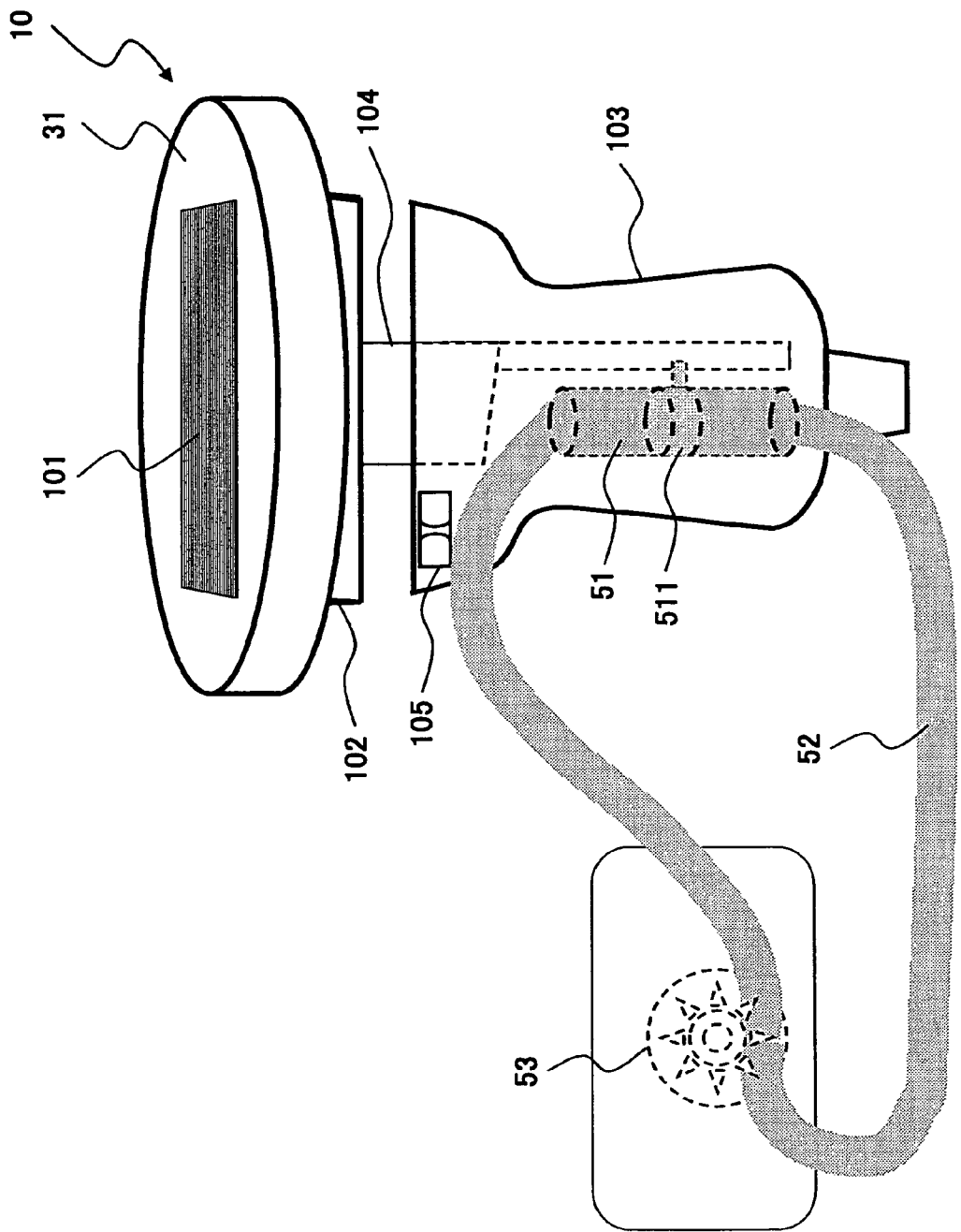
FIG. 5 is a diagram showing an ultrasound probe including an automatic pressing mechanism of a pump mechanism.

As another embodiment of the automatic pressing mechanism 20, FIG. 5 shows an example using driving force applied by a pump mechanism. In FIG. 5, the automatic pressing mechanism 20 is constituted of a reciprocating cylinder 51 stored in the probe holding part 103 of the ultrasound probe 10 held by the operator. The support member 104 of the pressing stage 102 is connected to a piston 511 of the cylinder 51. The cylinder 51 is connected to a pump 53 via a tube 52, and the piston 511 in the cylinder 51 is moved up and down by the pressure control of the pump 53. With this structure linked to the piston, the pressing stage 102 is automatically moved up and down. The switch 105 is an interface which allows the operator to operate the automatic pressing mechanism 20 (pump 53). The switch 105 is disposed on a position where the switch 105 is operable with fingers of the operator who holds the probe holding part 103. The working fluid of the pump mechanism is not particularly limited. Water, oil, air or the like may be used.

In the foregoing embodiment, a motor mechanism for driving the pressing stage 102 and a driving mechanism such as a pump mechanism are provided on the side of the probe holding part 103. The driving mechanism may be provided on the side of the pressing stage 102. The above explanation described that the ultrasound probe 10 includes the automatic pressing mechanism 20. The automatic pressing mechanism 20 may be attached to the outside of an existing ultrasound probe.

Figure 6:
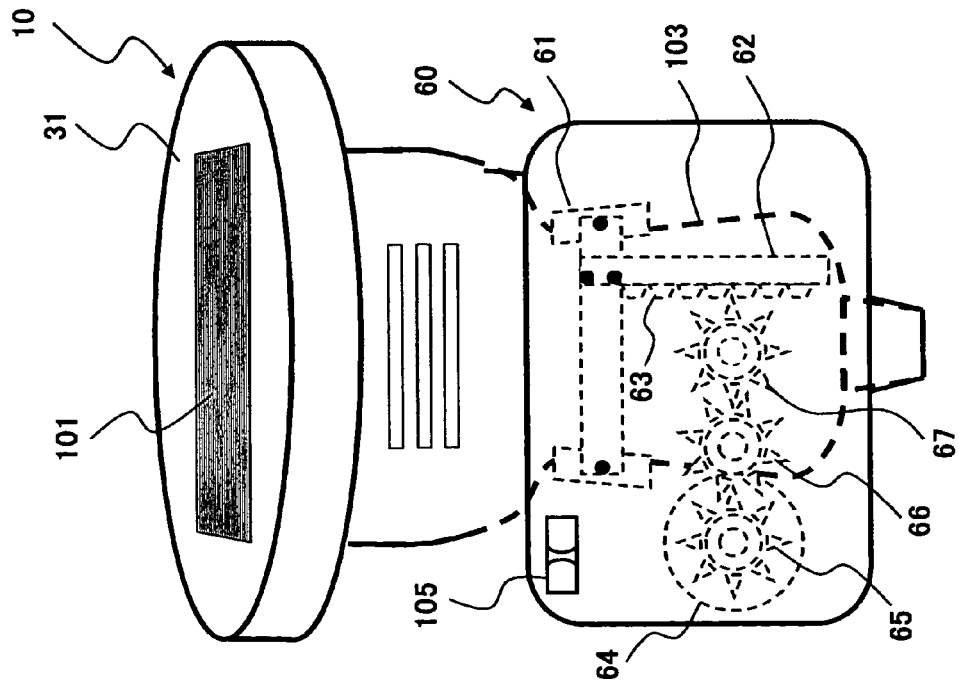
FIG. 6 is a diagram showing an ultrasound probe where an automatic pressing unit is attached.

FIG. 6 is a diagram showing another embodiment of the automatic pressing mechanism 20 in which an operation similar to the driving of the pressing stage can be performed by attaching an automatic pressing unit 60 to the outside of an existing ultrasound probe. The automatic pressing unit 60 comprises an ultrasound probe fixing mechanism 61 for holding the existing ultrasound probe 10 in a fixing manner and a driving mechanism 62 for linearly (vertically) driving the ultrasound probe fixing mechanism 61. The switch 105 is an interface which allows the operator to operate the automatic pressing mechanism 60. The switch 105 is disposed on a position where the switch 105 is operable with fingers of the operator who holds the automatic pressing unit 60. The ultrasound probe fixing mechanism 61 comes into contact with the neck of the probe holding part 103 of the ultrasound probe 10 and holds the ultrasound probe 10 in a fixing manner. The ultrasound probe 10 fixed thus by the ultrasound probe fixing mechanism 61 is similar to the pressing stage of FIG. 4. The probe holding part 103, that is, the ultrasound probe 10 is moved up and down using a rack and pinion constituted of a rack 63 on the support member 62 of the ultrasound probe fixing mechanism 61 and a pinion 65 on the rotating shaft of a driving mechanism (motor mechanism) 64. In FIG. 6, two gears 66 and 67 for power transmission are provided between the rack 63 and the pinion 65. A casing including the automatic pressing unit 60 is detachably attached outside the casing of the existing ultrasound probe 10. When the operator holds the automatic pressing unit 60, the ultrasound probe 10 can be moved up and down as a pressing stage.

Figure 7:
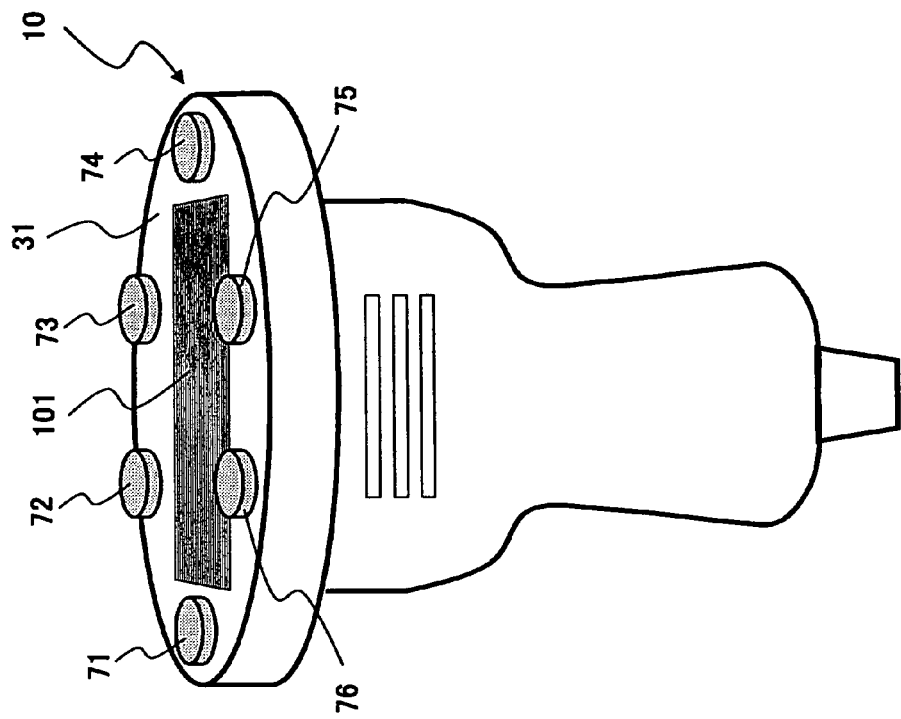
FIG. 7 is a diagram showing an ultrasound probe comprising a pressure sensor.

The following will describe an embodiment in which a pressure applied from the pressing surface to the skin of the subject 1 is measured by the pressure measuring section 210 and the operations of the automatic pressing mechanism 20 are controlled using pressure data. FIG. 7 is a diagram showing an embodiment of the ultrasound probe 10 comprising the pressure measuring section 210 for measuring a pressure applied between the ultrasound wave transmit/receive surface 101 of the ultrasound probe 10 and the skin of the subject 1. As shown in FIG. 7, the ultrasound probe 10 comprises the pressure measuring section 210 composed of pressure sensors 71 to 76 disposed on the edge of the pressing plate 31. As shown in FIG. 1, a pressure between the pressing plate 31 and the skin of the subject 1 is measured in a given time phase by using the ultrasound probe 10. Pressure data is outputted to the automatic pressing mechanism 20 and the distortion/elasticity modulus calculating section 211. In other words, the automatic pressing mechanism 20 of the present embodiment obtains pressure data measured by the pressure measuring section 210 and controls the pressing operation of the automatic pressing mechanism 20 according to the pressure data. The pressure measuring section 210 may obtain pressure data by measuring a load applied to the driving mechanism of the automatic pressing mechanism 20 and calculating, according to the load, a pressure applied from the pressing surface to the skin of the subject 1.

Figure 8:
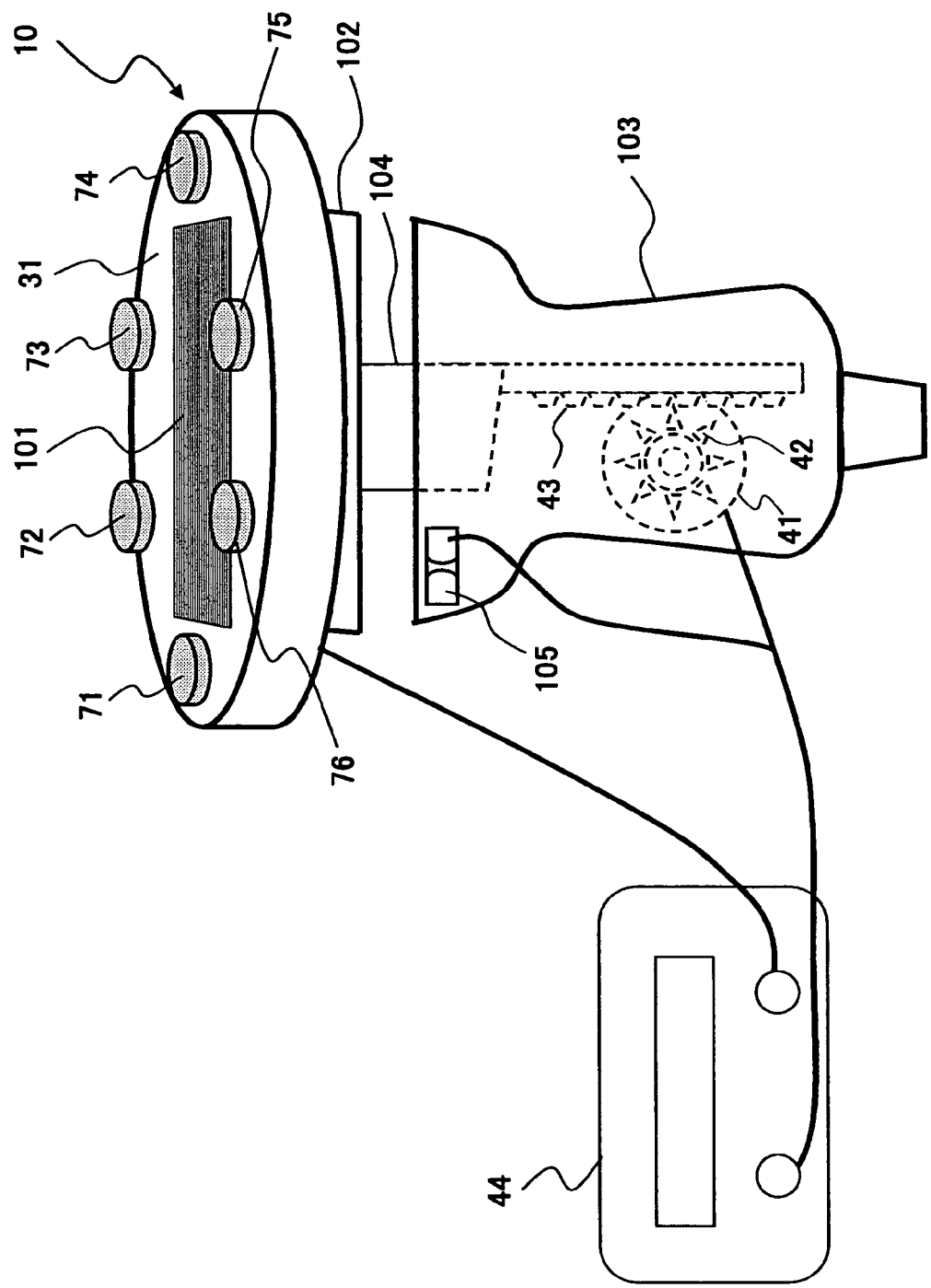
FIG. 8 is a diagram for explaining the control of the automatic pressing mechanism according to pressure information obtained by a pressure measuring section.

The following will describe the case where the automatic pressing mechanism 20 and the pressure measuring section 210 are connected to each other as shown in FIG. 1 and the operations thereof are controlled. FIG. 8 is a diagram showing an example of the automatic pressing mechanism 20 using driving force applied by the motor mechanism 41 of FIG. 4. As shown in FIG. 8, the pressure data of the pressure sensors 71 to 76 disposed on the edge of the pressing plate 31 is inputted to the motor control section 44 of the automatic pressing mechanism 20. The motor control section 44 outputs a motor control signal corresponding to the pressure data to the motor mechanism 41 and controls the motor mechanism 41 to perform a desired pressing operation.

The automatic pressing mechanism 20 of the present embodiment makes it possible to stop the operation of the automatic pressing mechanism 20 when the pressure measuring section 210 receives a pressure equal to or larger than a reference pressure, so that an excessive pressure is not applied to the subject. In the case of an elastic image, it is known that a pressure range enabling a high-quality elastic image is present and a pressure exceeding the upper limit value or a pressure lower than the lower limit value disturbs an elastic image. According to the automatic pressing mechanism 20 of the present embodiment, when the pressure measuring section 210 measures a pressure equal to or larger than a threshold value in a continuous pressing process, the operations of the automatic pressing mechanism 20 can be controlled to switch the pressing process to a continuous decompressing process. Conversely, when the pressure measuring section 210 measures a pressure equal to or smaller than a threshold value in a continuous decompressing process, the operations of the automatic pressing mechanism 20 can be controlled to switch the decompressing process to a continuous pressing process. A proper pressing state can be kept all the time by repeating these operations. Hence, it is possible to efficiently obtain a high-quality elastic image in a limited imaging time.

The following will describe an intra-corporeal ultrasound probe for obtaining an elastic image of the subject by using ultrasound waves according to the embodiment of the present invention. Oral, transanal, transvaginal, and endovascular ultrasound probes are available for parts of the subject where the ultrasound probe is inserted. The present invention is applicable to any type of the ultrasound probes. A transrectal probe inserted into a rectum through the anus of the subject will be discussed below as an example.

Figure 9:
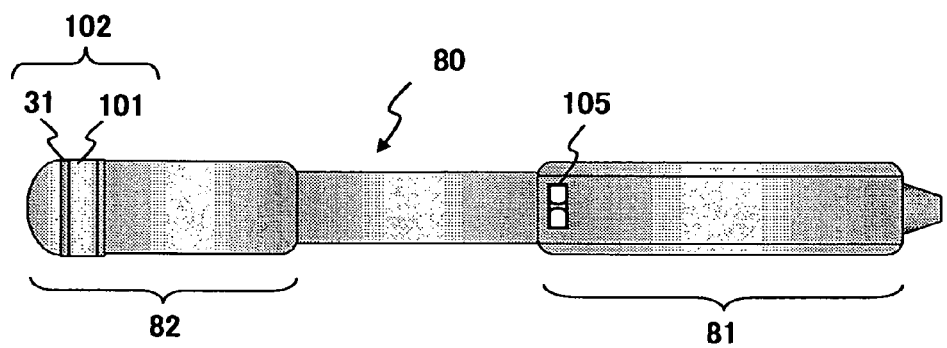
FIG. 9 is an outside drawing of a transrectal ultrasound probe according to the embodiment of the present invention.

FIG. 9 is an outside drawing of a transrectal ultrasound probe 80 according to the embodiment of the present invention. When the operator holds a probe holding part 81 and inserts an insertion part 82 into the rectum of the subject, the ultrasound wave transmit/receive surface 101 comes into contact with the inner surface of the rectum of the subject. The pressing stage 102 comprising the pressing surface constituted of the ultrasound wave transmit/receive surface 101 and the pressing plate 31 can move relative to the insertion part 82. The pressing stage 102 is pressed to the inner surface of the rectum of the subject by the automatic pressing mechanism 20. The switch 105 is an interface which allows the operator to operate the automatic pressing mechanism. The switch 105 is disposed on a position where the switch 105 is operable with fingers of the operator who holds the probe holding part 81.

Figure 10A:
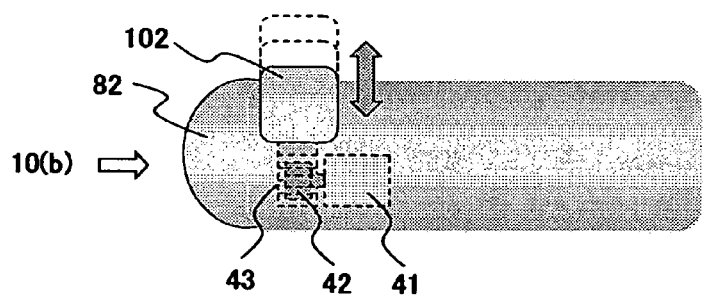
FIGS. 10(a) and 10(b) are diagrams showing an embodiment of the automatic pressing mechanism included in the transrectal ultrasound probe.
Figure 10B:
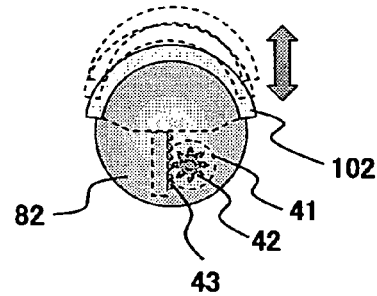

FIG. 10(a) is a diagram showing an embodiment of the automatic pressing mechanism 20 included in the transrectal ultrasound probe 80. FIG. 10(b) is a diagram showing the transrectal ultrasound probe 80 of FIG. 10(a) in the direction of an arrow 10(b). In this embodiment, as in the embodiment shown in FIG. 4, the action of the actuator including the motor mechanism 41, the pinion 42, and the rack 43 moves up and down moves the pressing stage 102 relative to the insertion part 82 in FIG. 10(b). At this point, the insertion part 82 has a surface opposite from the pressing stage 102 and the surface is in contact with, as a support surface, an inner surface of the rectum of the subject. The inner surface is opposite from an inner surface facing an imaging target. Thus, when the actuator changes a distance between the pressing stage 102 and the support surface, a pressure is applied to the inner surface where the pressing stage 102 is in contact with the rectum of the subject.

Figure 11A:
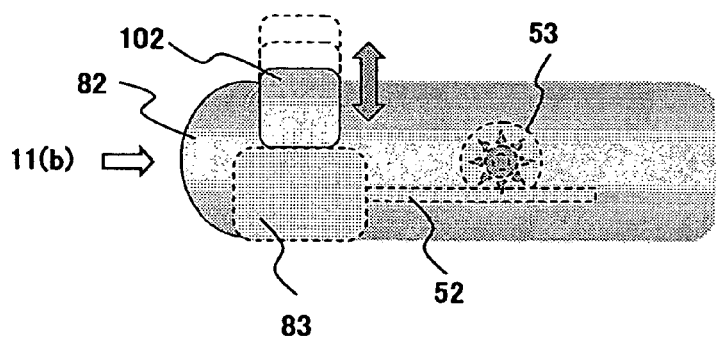
FIGS. 11(a) and 11(b) are diagrams showing another embodiment of the automatic pressing mechanism included in the transrectal ultrasound probe.
Figure 11B:
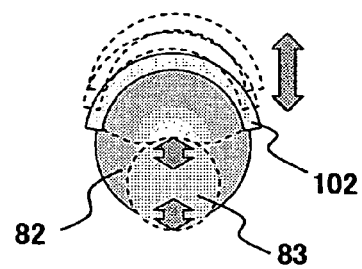

FIG. 11(a) is a diagram showing another embodiment of the automatic pressing mechanism 20 included in the transrectal ultrasound probe 80. FIG. 11(b) is a diagram showing the ultrasound probe 80 of FIG. 11(a) in the direction of an arrow 11(b). In this embodiment, a fluid is supplied or discharged to and from a bag 83 by a pump 53 and a tube 52, which are similar to those of the embodiment shown in FIG. 5, to expand or shrink the bag 83. Thus, the pressing stage 102 is vertically moved relative to the insertion part 82 in FIG. 11(a) and a pressure is applied to an inner surface of the rectum of the subject. The pressing stage 102 is in contact with the inner surface.

Figure 12A:
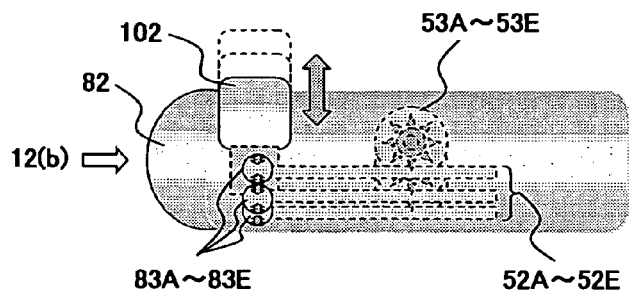
FIGS. 12(a) and 12(b) are diagrams showing another embodiment of the automatic pressing mechanism included in the transrectal ultrasound probe.
Figure 12B:
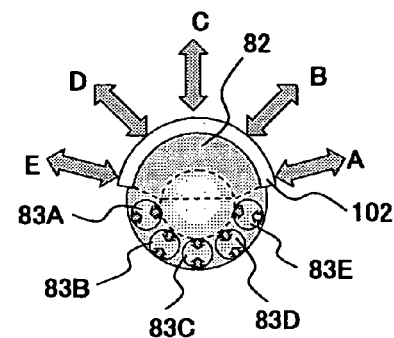

FIG. 12(a) is a diagram showing another embodiment of the automatic pressing mechanism 20 included in the transrectal ultrasound probe 80. FIG. 12(b) is a diagram showing the ultrasound probe 80 of FIG. 12(a) in the direction of an arrow 12(b). In this embodiment, five systems of pumps, tubes, and bags are provided as in the embodiment of FIGS. 11(a) and 11(b). Bags 83A, 83B, 83C, 83D, and 83E are expanded and shrunk by pumps 53A, 53B, 53C, 53D, and 53E and tubes 52A, 52B, 52C, 52D, and 52E. The bags 83A, 83B, 83C, 83D, and 83E are selectively expanded and shrunk, so that the pressing stage 102 can move relative to the insertion part 82 in the directions of arrows A, B, C, D, and E of FIG. 12(b). Thus, it is possible to apply a pressure to the inner surface of the rectum of the subject in a direction desired by the operator.

Figure 13A:
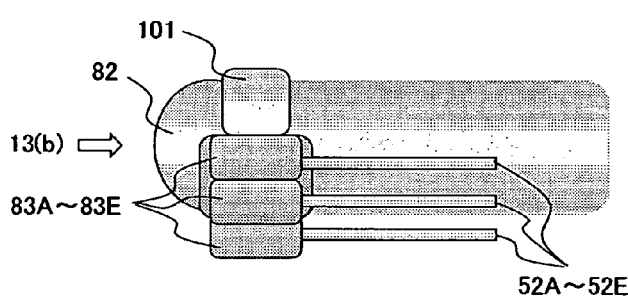
FIGS. 13(a) and 13(b) are diagrams showing another embodiment of the automatic pressing mechanism included in the transrectal ultrasound probe.
Figure 13B:
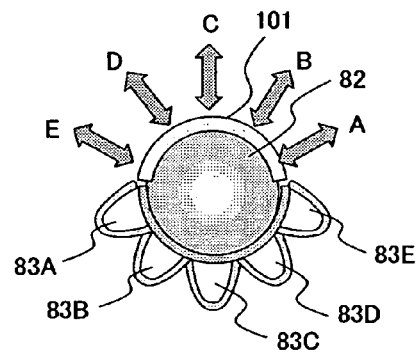

FIG. 13(a) is a diagram showing another embodiment of the automatic pressing mechanism 20 included in the transrectal ultrasound probe. FIG. 13(b) is a diagram showing the ultrasound probe of FIG. 13(a) in the direction of an arrow 13(b). In this embodiment, bags 83A, 83B, 83C, 83D, and 83E are attached outside an existing transrectal ultrasound probe as in the embodiment shown in FIGS. 12(a) and 12(b), and the bags are expanded and shrunk by five pumps (not shown) connected via tubes 52A, 52B, 52C, 52D, and 52E. The surfaces of the bags 83A, 83B, 83C, 83D, and 83E act as support surfaces coming into contact with an inner surface of the rectum of the subject. The inner surface is opposite from an inner surface facing an imaging target. The bags 83A, 83B, 83C, 83D, and 83E are selectively expanded and shrunk, so that the inserted part 82 can be entirely moved relative to the rectum of the subject in the directions of arrows A, B, C, D, and E shown in FIG. 13(b). Thus, even when the transrectal ultrasound probe has no movable pressing stage, it is possible to apply a pressure to the inner surface of the rectum of the subject in a direction desired by the operator.

Figure 14A:
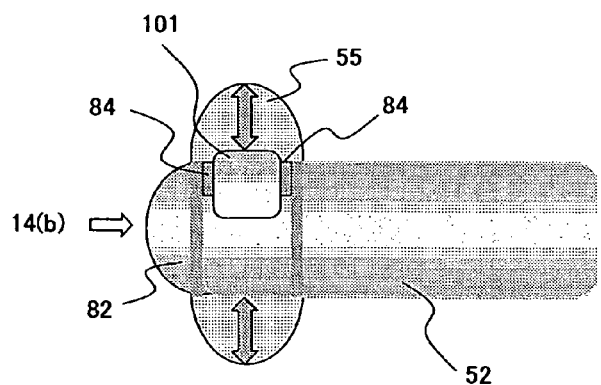
FIGS. 14(a) and 14(b) are diagrams showing another embodiment of the automatic pressing mechanism included in the transrectal ultrasound probe.
Figure 14B:
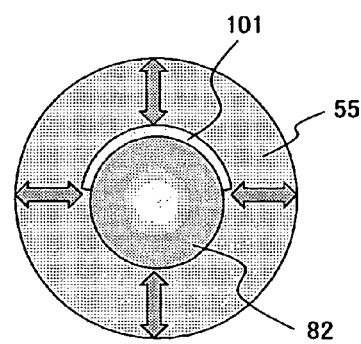

FIG. 14(a) is a diagram showing another embodiment of the automatic pressing mechanism 20 included in the transrectal ultrasound probe. FIG. 14(b) is a diagram showing the ultrasound probe of FIG. 14(a) in the direction of an arrow 14(b). In this embodiment, a ring-like bag 55 is attached outside an existing transrectal ultrasound probe, and a liquid (e.g., water, a physiological saline solution and so on) is supplied and discharged to and from the bag 55 by a pump (not shown) connected via an opening 84 and a tube 52, so that the bag 55 is expanded and shrunk. The bag 55 is in contact with the inner surface of the rectum of the subject. Thus, by expanding and shrinking the bag 55, a pressure can be applied to the inner surface of the rectum of the subject without moving the ultrasound wave transmit/receive surface 101 relative to the inner surface of the rectum of the subject. The bag 55 is interposed between the ultrasound wave transmit/receive surface 101 and the inner surface of the rectum of the subject. The bag 55 is filled with liquid and thus does not interfere with transmission/reception of ultrasound waves. A surface of the bag 55 comes into contact with an inner surface of the rectum in the direction of an imaging target of the subject and acts as an ultrasound wave transmit/receive surface. Another surface of the bag 55 comes into contact with an inner surface of the rectum of the subject, the inner surface being opposite from the inner surface facing the imaging target. Another surface of the bag 55 acts as a support surface.

Figure 15A:
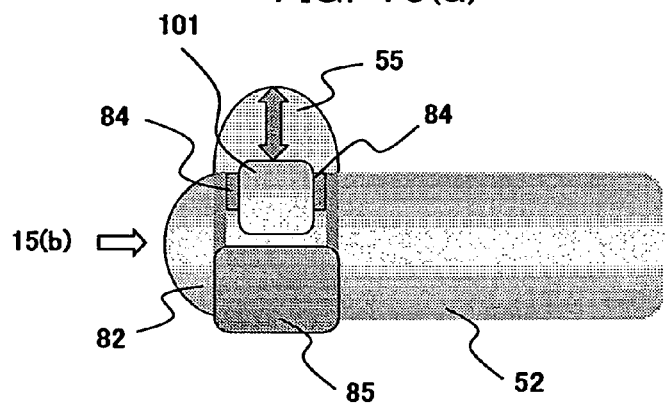
FIGS. 15(a) and 15(b) are diagrams showing another embodiment of the automatic pressing mechanism included in the transrectal ultrasound probe.
Figure 15B:
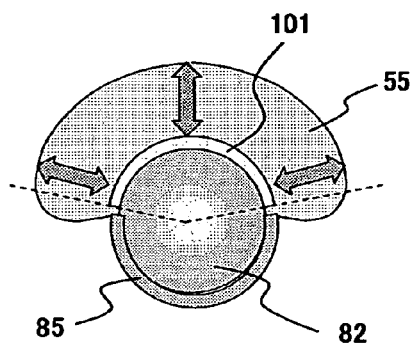

FIG. 15(a) is a diagram showing another embodiment of the automatic pressing mechanism 20 included in the transrectal ultrasound probe. FIG. 15(b) is a diagram showing the ultrasound probe of FIG. 15(a) in the direction of an arrow 15(b). In this embodiment, a stopper 85 is attached outside the ring-like bag 55 shown in FIGS. 14(a) and 14(b). With this configuration, it is possible to regulate the expanding direction of the bag 55 and efficiently apply a pressure to the inner surface of the rectum of the subject. At this point, a surface of the stopper 85 comes into contact with an inner surface of the rectum of the subject. The inner surface is opposite from an inner surface facing an imaging target. The surface of the stopper 85 acts as a support surface.

Figure 16A:
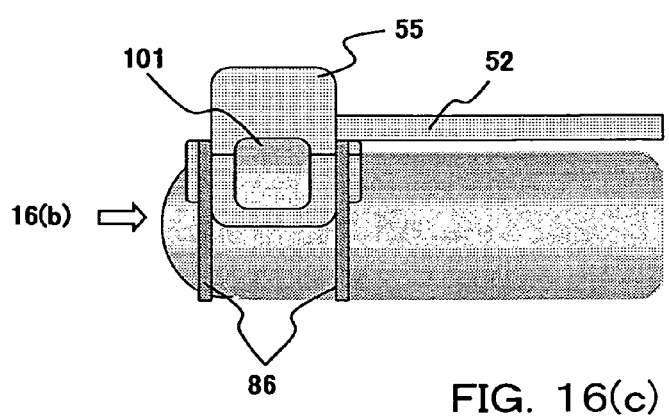
FIGS. 16(a), 16(b) and 16(c) are diagrams showing another embodiment of the automatic pressing mechanism included in the transrectal ultrasound probe.
Figure 16B:
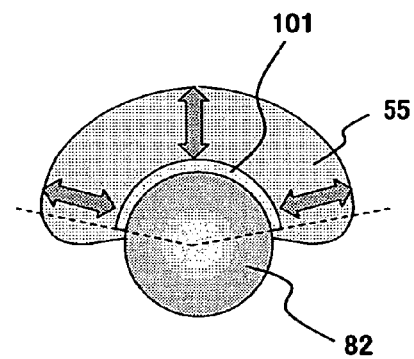
Figure 16C:
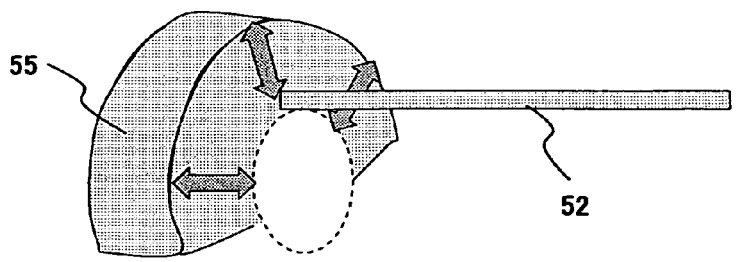

FIG. 16(a) is a diagram showing another embodiment of the automatic pressing mechanism 20 included in the transrectal ultrasound probe. FIG. 16(b) is a diagram showing the ultrasound probe of FIG. 16(a) in the direction of an arrow 16(b). FIG. 16(c) is a perspective view showing a bag 55 and a tube 52. In this embodiment, the bag 55 is attached outside an existing transrectal ultrasound probe with a fixing belt 86, and a liquid (water, a physiological saline solution, and so on) is supplied and discharged to and from the bag 55 by a pump (not shown) connected via the tube 52, so that the bag 55 is expanded and shrunk. The bag 55 is in contact with the inner surface of the rectum of the subject. Thus, by expanding and shrinking the bag 55, a pressure can be directly applied to the inner surface of the rectum of the subject. Hence, the automatic pressing mechanism 20 can be attached to the transrectal ultrasound probe which does not comprise the opening 84 (FIG. 15(a)) and the tube 52.

Figure 17:
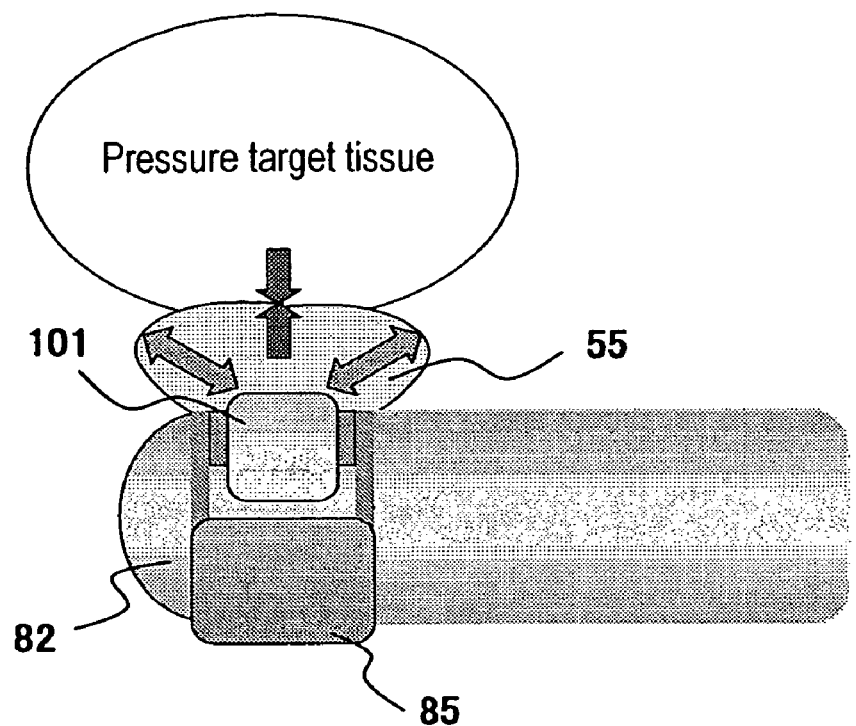
FIG. 17 is a diagram showing an example of the operation of a bag shown in FIG. 15(a)
Figure 18:
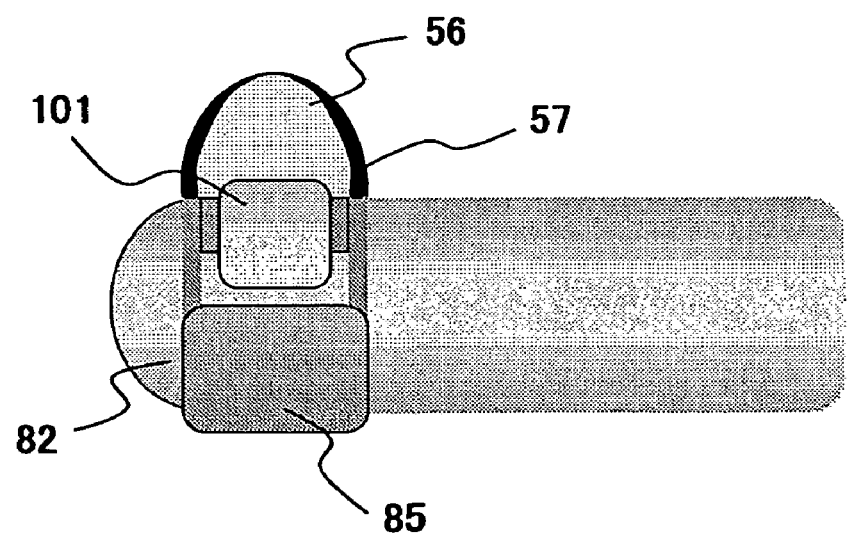
FIG. 18 is a diagram showing another embodiment of the bag.

FIG. 17 is a diagram showing an example of the operations of the bag 55 shown in FIG. 15(a). FIG. 18 is a diagram showing another embodiment of the bag. According to the shape and elasticity of a tissue to be pressed by the bag 55, the bag 55 may be deformed in the lateral direction of FIG. 17 in an expanding manner and a pressure may be applied to the target tissue with low efficiency. Thus, a bag 56 of FIG. 18 comprises a shell 57 for regulating the expanding direction of the bag 56. The shell 57 requires lower elasticity than other parts of the bag 56. For example, the shell 57 is formed by the following methods: the shell 57 is made thicker than the other parts of the bag 56, a net or the like is bonded to a part of the bag 56 so as to correspond to the shell 57, or the shell 57 is formed of a different material having lower elasticity than the other parts of the bag 56. Thus, it is possible to efficiently apply a pressure to a target tissue.

In the above-described intra-corporeal ultrasound probe, the pressure measuring section 210 (FIG. 1) for measuring a pressure applied from the pressing surface to the subject and outputting pressure data may be constituted of the pressure sensors provided on the edge of the ultrasound wave transmit/receive surface 101 as shown in FIG. 7. The pressure measuring section 210 may obtain pressure data by measuring a load applied to the driving mechanism of the automatic pressing mechanism 20 and calculating, according to the load, a pressure applied from the pressing surface to the subject. When the automatic pressing mechanism 20 comprises a bag and a tube, the pressure measuring section 210 may obtain pressure data by measuring the internal pressure of the bag or the tube.

In the intra-corporeal ultrasound probe, in the case where the actuator changes a distance between the probe holding part 81 and the ultrasound wave transmit/receive surface 101, even when the support surface is not in contact with a surface opposite from a surface facing an imaging object of the subject, a pressure can be applied to the subject.

With the automatic pressing mechanism 20 of the foregoing embodiment, it is possible to automatically apply a pressure to the subject at a desired constant speed in a fixed direction, thereby obtaining elastic image data with high image quality at a given time. Further, it is possible to keep reproducibility of a pressing operation.

The following will describe the display value evaluating section 215 of the present embodiment. The display value evaluating section 215 uses displacement frame data outputted from the displacement measuring section 209, evaluates the value of image display for each measuring point in ROI, distinguishes between useless information and useful information, and does not leave an image of the useless information (masks the useless information) in the end.

Figure 19:
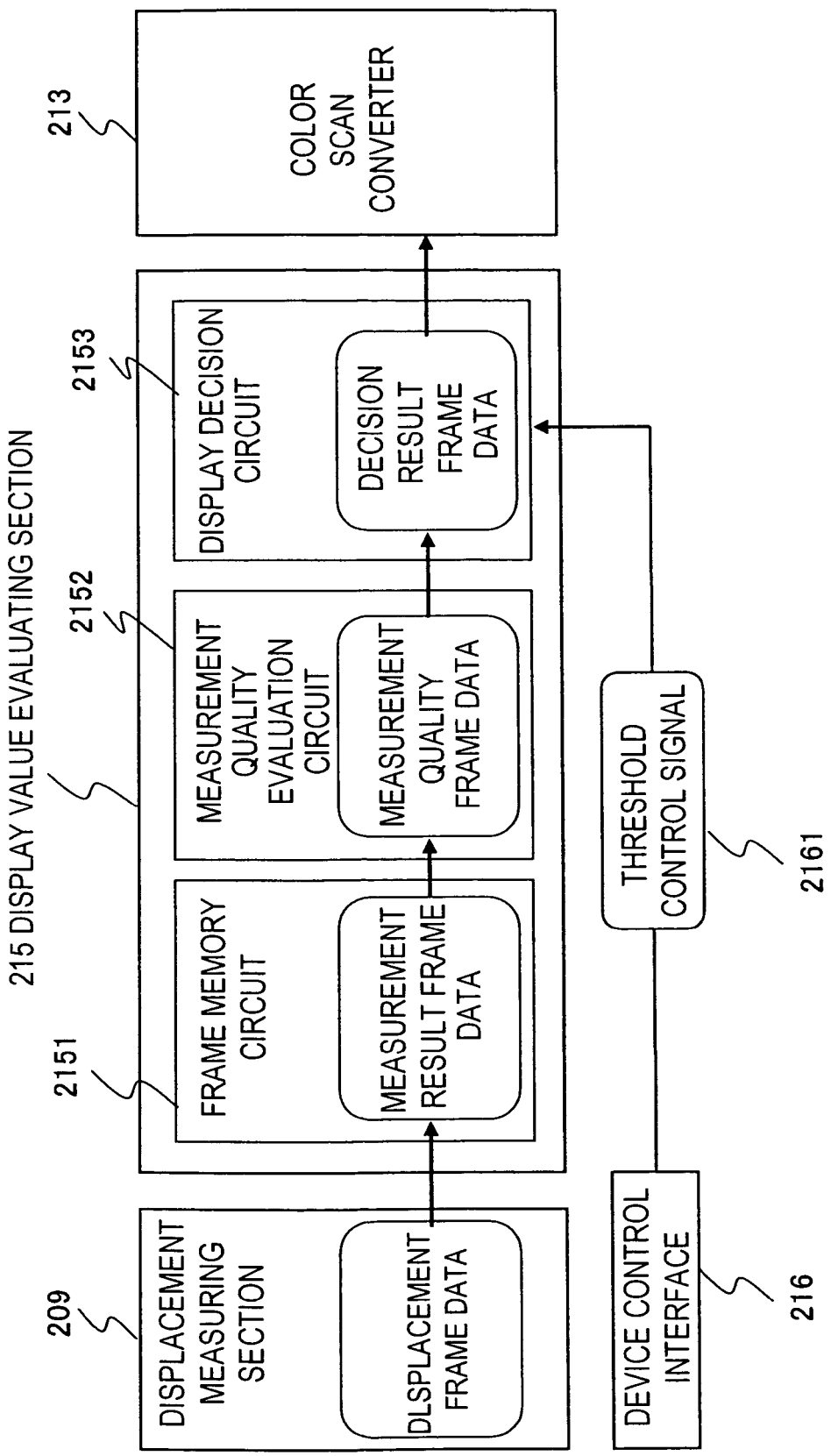
FIG. 19 is a block diagram showing an embodiment of a display value evaluating section shown in FIG. 1.

FIG. 19 is a diagram showing an example of the flow of data inputted and outputted in the display value evaluating section 215 of the present invention. The display value evaluating section 215 comprises a frame memory circuit 2151, a measurement quality evaluation circuit 2152, and a display decision circuit 2153.

The frame memory circuit 2151 obtains, as measurement result frame data, displacement frame data outputted from the displacement measuring section 209, and outputs the data to the measurement quality evaluation circuit 2152. The measurement quality evaluation circuit 2152 receives the measurement result frame data outputted from the frame memory circuit 2151 and constructs measurement quality frame data which reflects, as a numeric value, reliability of the measurement result frame data, that is, whether a measurement result is normal or not on each measuring point in ROI.

Figures 20, 21:
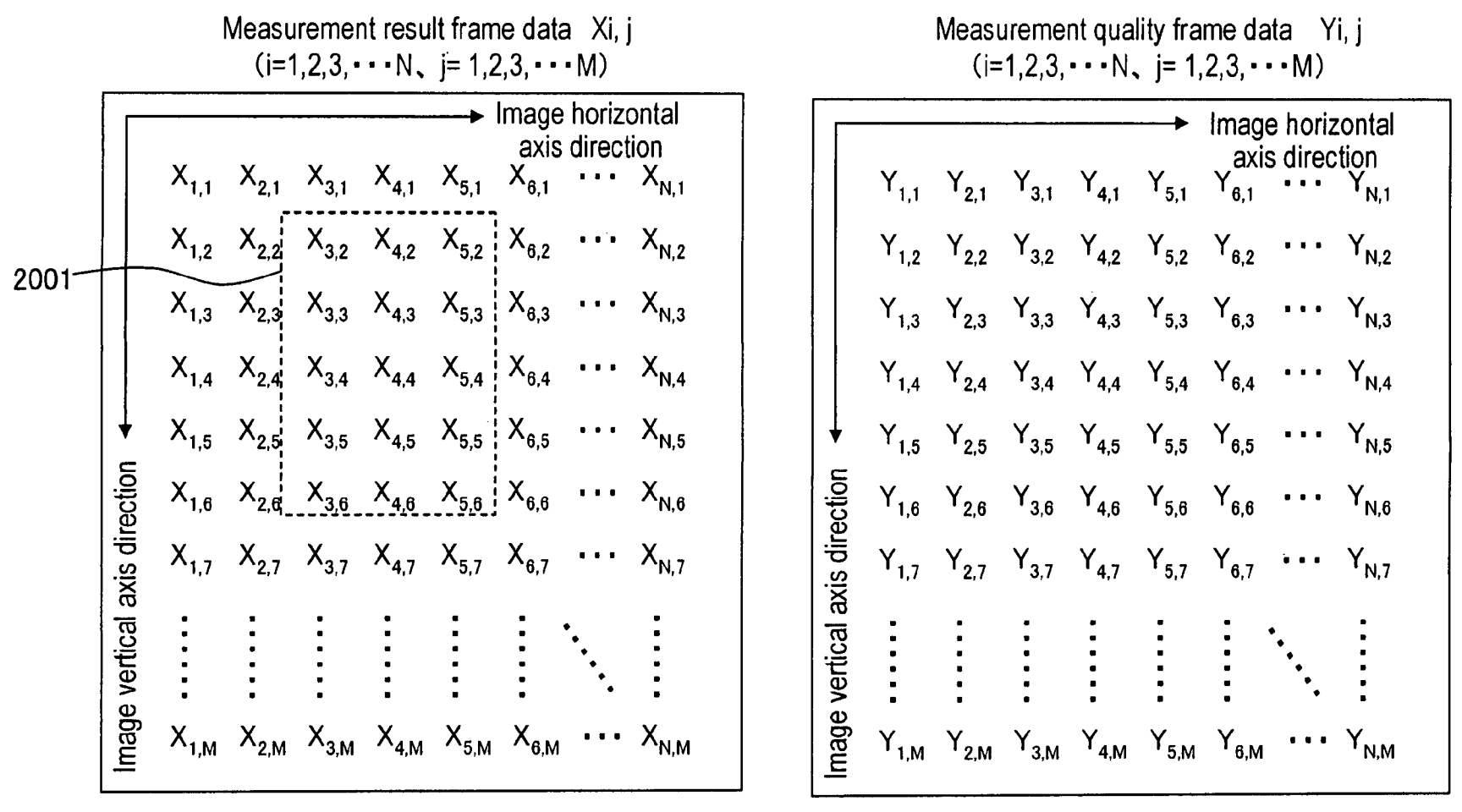

The following will discuss an example of the operations of the measurement quality evaluation circuit 2152. The measurement quality evaluation circuit 2152 performs statistical processing in which a population is the element data of measurement result frame data, and constructs measurement quality frame data including a statistical characteristic amount as element data. FIG. 20 is a diagram showing an example in which measurement quality frame data is constructed based on a statistical characteristic amount.

First, as shown in FIG. 20, the element data of measurement result frame data is represented as $X_{i,j}$ (i=1, 2, 3, ..., N, j=1, 2, 3 ..., M). An index i corresponds to a coordinate in the horizontal axis direction of an elastic image and an index j corresponds to a coordinate in the vertical axis direction. All element data included in ROI set by the ultrasound apparatus are referred to with these indexes.

When element data, e.g., $X_{4,4}$ is currently noticed and a kernel 2001 of 3 (elements)×5 (elements) is set with coordinates $X_{4,4}$ disposed at the center. As a statistical characteristic amount with a population of 15 element data in total distributed in the kernel 2001, for example, an average and a standard deviation are calculated as below:

$$(\text{average})_{4,4} = \{\Sigma(\text{measurement result frame data } X_{i,j})\}^2/15 \{(\text{standard deviation})_{4,4}\}^2 = \Sigma\{(\text{average})_{4,4} - (\text{measurement result frame data } X_{i,j})\}^2/15$$

$(3 \leq i \leq 5, 2 \leq j \leq 6)$

According to the above steps, $(\text{Standard deviation})_{i,j}$ is similarly calculated for each element data $X_{i,j}$, input is set as below according to each element data $Y_{i,j}$ of measurement quality frame data, and measurement quality frame data of FIG. 21 is generated.

$$(\text{measurement quality frame data } Y_{i,j}) = (\text{standard deviation})_{i,j}$$

(i=1, 2, 3, ..., N, j=1, 2, 3, ..., M)

Since displacement frame data is inputted as measurement result frame data, when an operation is performed and measurement quality frame data is constructed, element data $Y_{i,j}$ constituting the measurement quality frame data has element data $X_{i,j}$ of the same coordinates at the center in displacement frame data and is fed with a value reflecting variations in displacement (movement) with element data serving as a population. The element data is distributed in a region of a set kernel size. The above measurement quality frame data is outputted to the display decision circuit 2153.

Figure 22:
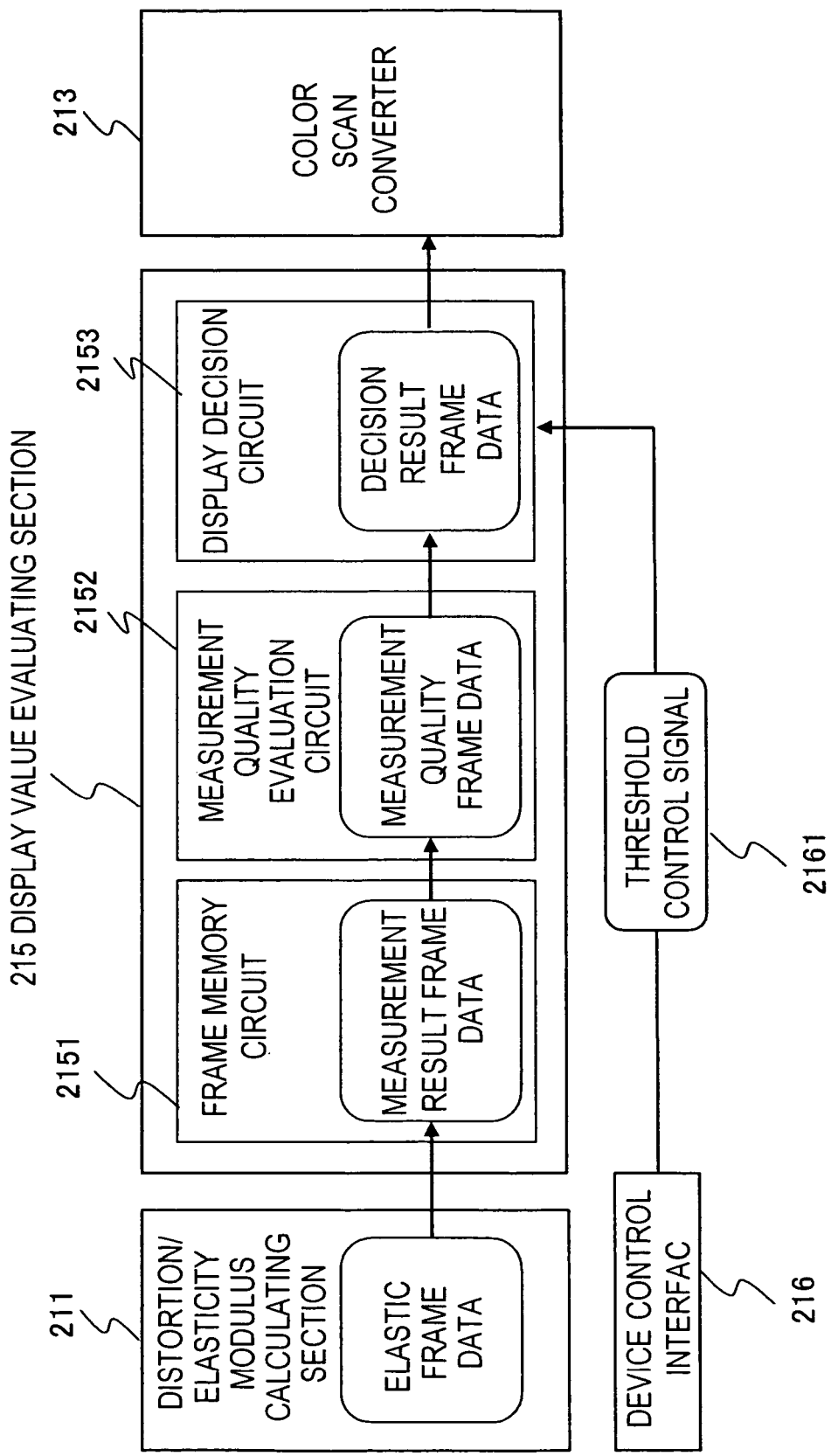
FIG. 22 is a block diagram showing another embodiment of the display value evaluating section shown in FIG. 1.

In the foregoing embodiment, displacement frame data is inputted as measurement result frame data in the display value evaluating section 215, and a region worth displaying and a region not worth displaying are evaluated. For example, as shown in FIG. 22, in the distortion/elasticity modulus calculating section 211, elastic frame data generated by performing spatial differentiation on displacement frame data may be inputted as measurement result frame data in the display value evaluating section 215. Since the elastic frame data reflects local discreteness of displacement frame data, it is possible to achieve the same operation. The size of the kernel 2001 can be set at random. Further, the size of the kernel 2001 may be small around ROI. Processing such as spatial smoothing and smoothing between frames in the time-axis direction may be performed on measurement quality frame data.

The display decision circuit 2153 is fed with measurement quality frame data outputted from the measurement quality evaluation circuit 2152, fed with a threshold control signal 2161 outputted from the control section of the ultrasound apparatus via the device control interface 216, and performs threshold processing in response to the threshold control signal 2161, so that decision result frame data indicating whether an image corresponding to a measuring point should be displayed or not is constructed. The decision result frame data is outputted to the color scan converter 213.

The following will describe an example of the operations of the display decision circuit 2153. The element data of measurement quality frame data reflects a standard deviation value of a displacement (movement) which is described in the explanation of the measurement quality evaluation circuit 2152. Thus, decision result frame data can be constructed by threshold decision on the element data of measurement quality frame data.

Regarding the element data of the measurement quality frame data generated by the measurement quality evaluation circuit 2152, as the element data of the measurement quality frame data increases in value, variations in displacement distributed in a fixed region increase with the coordinates of the element data at the center. Then, the display decision circuit 2153 sets, at a threshold value Th, the threshold control signal 2161 inputted from the ultrasound apparatus control section, and decides whether all element data constituting the measurement quality frame data are larger than the threshold value Th or not. For example, when element data $Y_{i,j}$ of the measurement quality frame data is larger than the threshold value Th, the display decision circuit 2153 sets "0" for element data $Z_{i,j}$ of the same coordinates of decision result frame data. When element data $Y_{i,j}$ is smaller than the threshold value Th, the display decision circuit 2153 sets "1" for the data $Z_{i,j}$. Input is set as follows:

$$(\text{measurement quality frame data } Y_{i,j}) > (\text{threshold value } Th) \Rightarrow (\text{decision result frame data } Z_{i,j}) = 0$$

$$(\text{measurement quality frame data } Y_{i,j}) \leq (\text{threshold value } Th) \Rightarrow (\text{decision result frame data } Z_{i,j}) = 1$$

(i=1, 2, 3, ..., N, j=1, 2, 3, ..., M)

Decision result frame data $Z_{i,j}$ generated as a result is, for example, configured as shown in FIG. 23.

With this threshold processing, decision result frame data is constructed in which "0" or "1" is inputted to all element data $Z_{i,j}$ and the decision result frame data is outputted to the color scan converter 213. FIG. 24 is a diagram showing an example of decision frame data $Z_{i,j}$ in which "0" or "1" is inputted to each element data $Z_{i,j}$.

In the foregoing embodiment, decision result frame data is generated in which a region worth displaying is set at "0" and a region not worth displaying is set at "1" in the display value evaluating section 215. The present invention is not limited to this example as long as the values are set so as to recognize whether a region is worth displaying or not.

Figure 25:
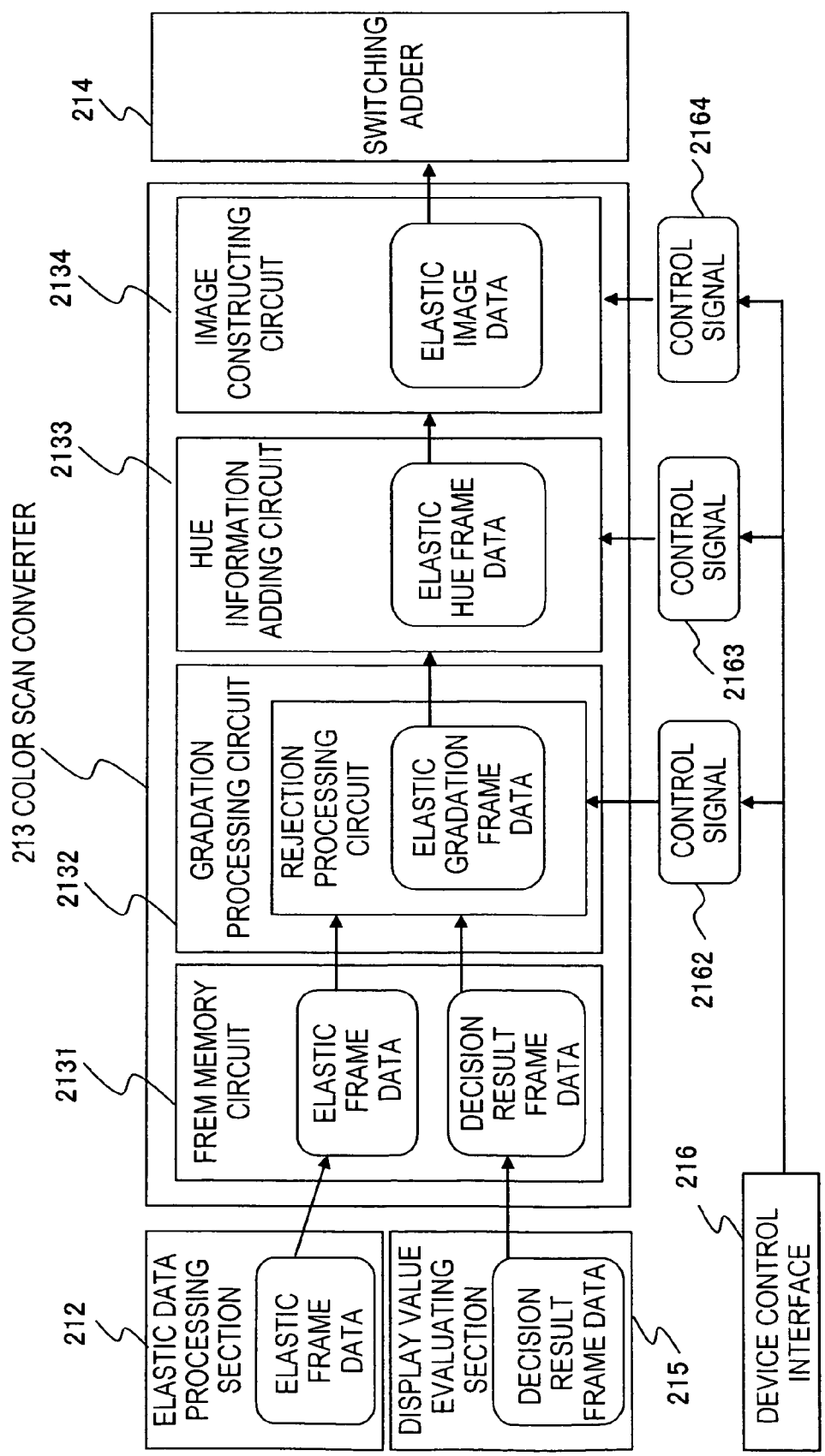
FIG. 25 is a block diagram showing an embodiment of a color scan converter shown in FIG. 1.

The following will discuss an example of the operations of the color scan converter 213 according to the present invention. FIG. 25 is a diagram showing an example of the flow of data inputted and outputted in the color scan converter 213 of the present invention. The color scan converter 213 comprises a frame memory circuit 2131, a gradation processing circuit 2132, a hue information adding circuit 2133, and an image constructing circuit 2134. The gradation processing circuit 2132 comprises a rejection processing circuit.

The frame memory circuit 2131 obtains decision result frame data outputted from the display value evaluating section 215 as well as elastic frame data outputted from the elastic data processing section 212, and outputs the data to the rejection processing circuit in the gradation processing circuit 2132.

The gradation processing circuit 2132 converts elastic frame data, which is outputted from the frame memory circuit 2131 and has continuous values, into elastic gradation frame data having discrete values (e.g., 8 bits, 256 levels). This processing is performed by the rejection processing circuit. The rejection processing circuit is fed with elastic frame data and decision result frame data from the frame memory circuit 2131, and sets information on corresponding elements of elastic gradation frame data according to information on the elements of decision result frame data.

The following will discuss an example of the operations of the rejection processing circuit in the gradation processing circuit 2132. In the element data of decision result frame data, as values of decision results described in the operations of the display value evaluating section 215, "0" is set for a region less worth displaying and "1" is set for a region worth displaying as shown in FIG. 24. In this case, the rejection processing circuit sets the element data of elastic gradation frame data of the corresponding coordinates at 8-bit values with 256 levels according to the values of the element data of the decision result frame data.

In this setting, when the element data of elastic frame data corresponds to coordinates having a value of 0 as the element data of decision result frame data, the element data of the elastic frame data is useless information. When the element data of elastic frame data corresponds to coordinates of "1", the element data is useful information. According to the decision results, when the element data of elastic gradation frame data corresponds to coordinates having a value of "0" as the element data of decision result frame data, "0" is set for the element data of the elastic gradation frame data regardless of whether the values of the element data of elastic frame data on the corresponding coordinates are large or not. When the element data of elastic gradation frame data corresponds to coordinates having a value of "1" as the element data of decision result frame data, values with 256 gray scales are set according to the values of the element data of the elastic frame data on the corresponding coordinates. That is, an operation is performed as below:

(decision result frame data $Z_{i,j}$) = 0

⇒ (elastic graduation frame data $T_{i,j}$) = 0

(decision result frame data $Z_{i,j}$) = 1

⇒ (elastice graduation frame data $T_{i,j}$) =

(values "1" to "255" corresponding to $S_{i,j}$)

($i$ = 1, 2, 3, ... , $N$, $j$ = 1, 2, 3, ... , $M$)

where $S_{i,j}$ represents the element data of elastic frame data inputted from the frame memory circuit to the rejection processing circuit, $Z_{i,j}$ represents decision result frame data, and $T_{i,j}$ represents the element data of elastic gradation frame data generated in the rejection processing circuit.

This gradation processing constructs elastic gradation frame data where "0" to "255" of 256 levels are inputted to all element data $T_{i,j}$. Elastic gradation frame data obtained by the gradation processing circuit 2132 is inputted to the hue information adding circuit 2133.

The hue information adding circuit 2133 is fed with elastic gradation frame data outputted from the gradation processing circuit and generates elastic hue frame data according to information on each element of the elastic gradation frame data. The following will describe an example of the operations of the hue information adding circuit 2133. In the element data of elastic gradation frame data, values are inputted as results of the operations of the display value evaluating section 215 and the gradation processing circuit 2132. For example, "0" is inputted for coordinates less worth displaying, and values from "1" to "255" of 255 levels are inputted for coordinates worth displaying. In the hue information adding circuit 2133, for example, processing is performed to set hue information for the element data of elastic hue frame data on the corresponding coordinates according to the values of the element data of elastic gradation frame data.

In this setting, when the element data of elastic frame data corresponds to coordinates having a value of 0 as the element data of elastic gradation frame data, the element data of the elastic frame data is useless information. When the element data of elastic frame data corresponds to coordinates of "1" to "255", the element data is useful information. According to the decision results, when the element data (R: red, G: green, B: blue) of elastic hue frame data corresponds to coordinates having a value of "0" as the element data of elastic gradation frame data, for example, black (R=0, G=0, B=0) is set as hue information. When the element data of elastic hue frame data corresponds to coordinates having values of "1" to "255" as the element data of elastic gradation frame data, for example, hue information of 255 levels from blue to red is set according to the values of the element data of the elastic gradation frame data on the corresponding coordinates.

That is, operations are performed as below:

(elastic gradation frame data $T_{i,j}$)=0
⇒(elastic hue frame data $U_{Ri,j}$)=0
(elastic hue frame data $U_{Gi,j}$)=0
(elastic hue frame data $U_{Bi,j}$)=0
(elastic gradation frame data $T_{i,j}$)=1 to 255
⇒(elastic hue frame data $U_{Ri,j}$)=($T_{i,j}$−1)
(elastic hue frame data $U_{Gi,j}$)=0
(elastic hue frame data $U_{Bi,j}$)=254−($T_{i,j}$−1)
($i$=1, 2, 3, ... , N, $j$=1, 2, 3, ... , M)

where $T_{i,j}$ represents the element data of elastic gradation frame data inputted from the gradation processing circuit 2132 to the hue information adding circuit 2133, and $U_{Ri,j}$, $U_{Gi,j}$, and $U_{Bi,j}$ represent the R (red) component, the G (green) component, and the B (blue) component of the element data of elastic hue frame data generated in the hue information adding circuit 2133.

Figure 26:
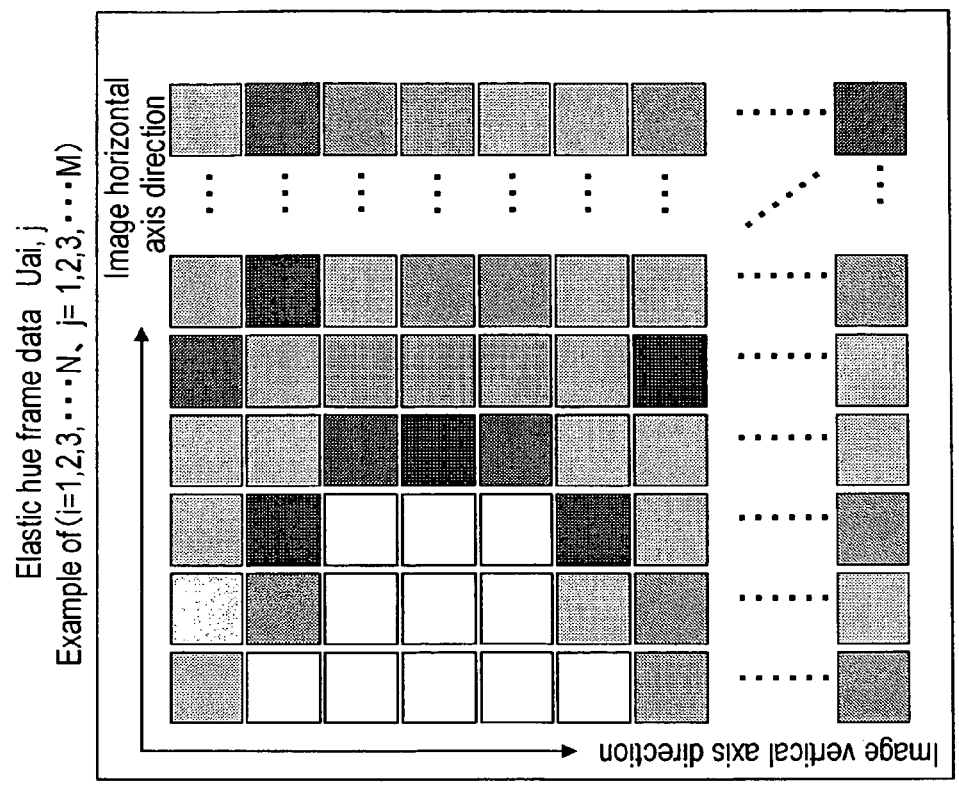
FIG. 26 is a diagram showing an example of elastic hue frame data constructed by a hue information adding circuit of FIG. 25.

For example, FIG. 26 shows elastic hue frame data $U_{ai,j}$ obtained by performing the above processing according to decision result frame data $Z_{i,j}$ of FIG. 23. In FIG. 26, hue information cannot be illustrated. Thus, regions corresponding to elastic gradation frame data $T_{i,j}$=0 are illustrated as white regions and regions corresponding to elastic gradation frame data $T_{i,j}$=1 to 255 are illustrated with gray scales according to the values of the regions. With the addition of hue information, elastic hue frame data can be constructed in which the values of hue information of R, G, and B are inputted to all element data $U_{ai,j}$. Elastic hue frame data to which hue information has been added by the hue information adding circuit 2133 is outputted to the image constructing circuit 2134 of the subsequent stage.

Figure 27:
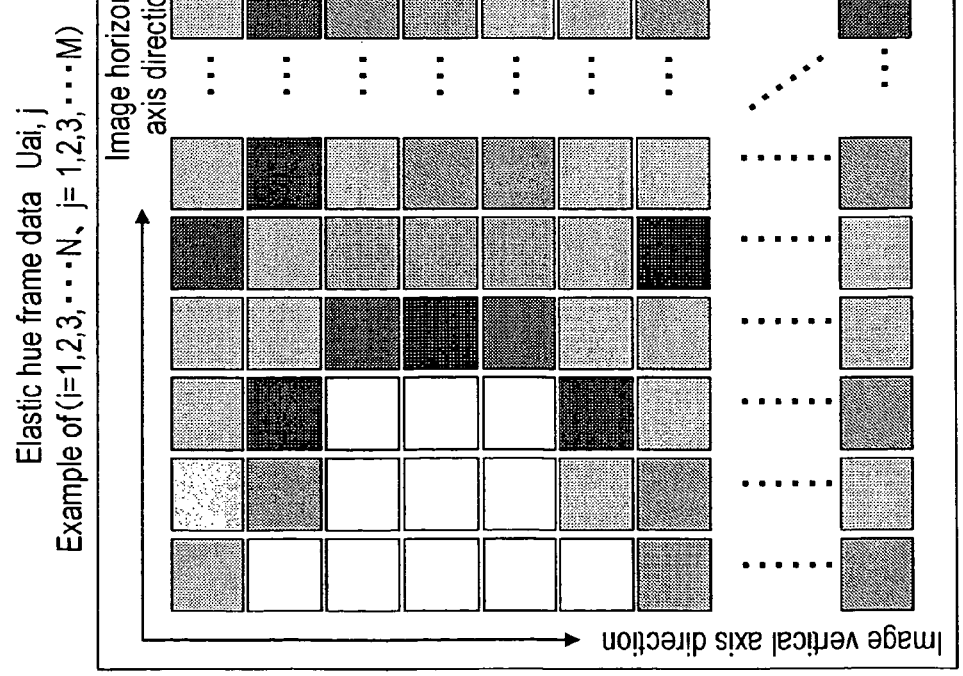
FIG. 27 is a diagram showing an example of the elastic hue frame data before processing when the position and range of ROI is automatically controlled.
Figure 28:
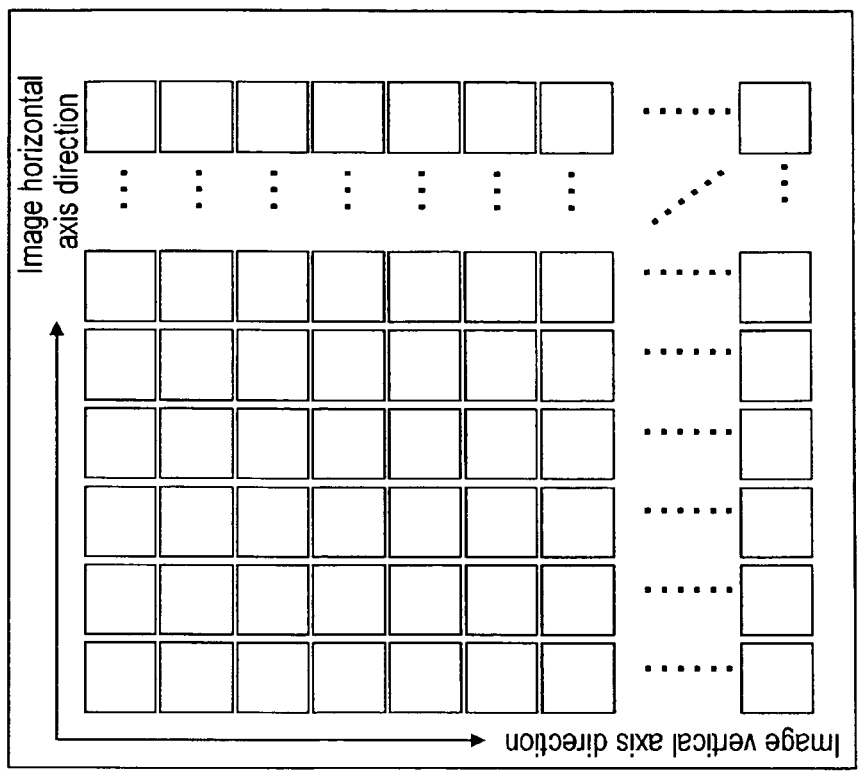
FIG. 28 is a diagram showing an example of the elastic hue frame data after processing when the position and range of ROI is automatically controlled.

In the present embodiment, regions worth displaying are displayed with gradation of blue to red and regions less worth displaying are displayed with a single color of black. The present invention is not limited to this example. A different method of allocating hues may be used as long as a region less worth displaying can be recognized as an image. For example, regions worth displaying may be displayed with gradation of yellow to green and regions less worth displaying may be displayed with a single color of blue. In the present embodiment, the components of elastic hue frame data were described using an RGB signal format. The present invention is not limited to this example and may be achieved by a method of adding hue information in another signal format (e.g., YUV). Further, although the present embodiment describes an example in which a region not worth displaying is identified with hue information different from that of a region worth displaying in ROI, the present invention is not limited to this example. For example, as shown in FIG. 27, when regions not worth displaying are continuously present in two rows on the left in the element data of elastic hue frame data $U_{bi,j}$, the part of the regions is evaluated as a removal region. When a part is evaluated as a removal region, the part is removed and ROI is reduced as shown in FIG. 28. ROI set and displayed by the ultrasound imaging apparatus is reduced, expanded, or moved, so that the removal region may be automatically removed out of an ROI range set by the apparatus. FIG. 28 shows an example in which two left rows corresponding to a region not worth displaying in FIG. 27 are removed and ROI is reduced.

The image constructing circuit 2134 is fed with elastic hue frame data outputted from the hue information adding circuit 2133 and fed with a control signal 2164 outputted from the control section of the ultrasound apparatus through the device control interface 216. Accordingly, image processing including interpolation such as polar coordinate conversion, scaling of an image, reversal and rotation of an image is performed on elastic hue frame data serving as original data, and elastic image data constituted of pixel data is generated. The image constructing circuit 2134, the gradation processing circuit 2132, and the hue information adding circuit 2133 are fed with the control signals 2162 to 2164 through the device control interface 216. Whether functions should be accepted or not is decided and the settings of operations are switched and changed according to the control signals.

Incidentally, ultrasound received signal frame data at a given time reflects the structure and arrangement of living tissues at that time as information. In a method of obtaining tissue elastic information with ultrasound waves, first, a pair of ultrasound received signal frame data obtained at regular intervals is used to calculate a displacement of each living tissue. The displacement is caused by a pressure (pressurization, decompression) of a living tissue between fixed time periods. Then, spatial differentiation is performed on displacement information, so that a distortion is calculated on each point in ROI set by the ultrasound apparatus and an image is constructed and displayed.

However, at the site of actual imaging, ROI set by the imaging apparatus may have an error (correlation operation error) region, in which a correct displacement cannot be calculated, due to an improper pressing direction or an excessive pressing speed, for example, in a first aspect where a tissue of interest is moved by a pressure in the short axis direction of the probe and placed out of a measuring cross section during a time interval when a pair of ultrasound received signal frame data is obtained, and in a second aspect where a tissue of interest is displaced by a pressure at high speed in the long axis direction or the pressing direction of the probe and placed out of a predetermined displacement operation range set by the imaging apparatus.

ROI set by the imaging apparatus may have an error (correlation operation error) region, in which a correct displacement cannot be calculated, due to the absence of a received signal reflecting a property of a tissue of interest with sufficient intensity, for example, in a third aspect where a deep region not reached by any transmitted ultrasound waves due to attenuation acts as a region of interest, and in a fourth aspect where a region with just a few ultrasound reflectors (a cyst and a lesion having a liquid therein) acts as a region of interest.

In the first to fourth aspects, a region set as a region of interest (ROI) is likely to include a region having an incorrectly calculated displacement. When a distortion calculated using the displacement is displayed as an image, the region of interest of the distortion image includes incorrect information.

ROI set by the imaging apparatus may include a region where a displacement is insignificantly calculated, due to the shape of the ultrasound probe and the pattern of a tissue of interest, for example, in a fifth aspect where a region of interest is a region where the ultrasound probe is not in contact with the subject. In the fifth aspect, a region set as a region of interest (ROI) includes a region having an insignificant displacement. When a distortion calculated using the displacement is displayed as an image, a distortion image similarly includes incorrect and insignificant information.

In aspects represented by the first to fifth aspects, a first region and a second region discussed below are observed as a result of a tissue displacement made by a pressure. The first region is a region where measuring points have equal displacements in the same direction (tissues are locally combined with one another and collectively displaced in the same direction), the second region is a region where a displacement and a direction vary between adjacent measuring points (tissues are not locally combined with one another and adjacent tissues are discretely displaced in various directions). The two first and second regions broadly classified thus are observed in one displacement frame data.

In the first to fifth aspects, a region with an incorrectly calculated displacement and a region with an insignificantly calculated displacement are varied, like the second region, in displacement and direction as displacement calculation results, and a region with a proper pressure becomes similar to the first region as a displacement calculation result.

The foregoing embodiment described that displacement frame data is used by the display value evaluating section 215 and the color scan converter 213. In these operations, the following series of operations is performed: displacement frame data is used to determine variations in local displacement, a measuring point with a large variation is evaluated as being less worth displaying, and a measuring point with a small variation is evaluated as being worth displaying. Hue information of black is added to a pixel of elastic image data corresponding to the coordinates of the measuring point evaluated as being less worth displaying, and hue information consecutively changed from blue to red is added to a pixel of elastic image data corresponding to the coordinates of the measuring point evaluated as being worth displaying, according to the value of an element of the corresponding coordinates of measured elastic frame data. An elastic image is displayed on the screen of the ultrasound imaging apparatus. In the elastic image, elastic image information on the measuring point less worth displaying is removed and a hue is added only to the measuring point worth displaying. Hence, only a region where a proper pressure is applied is displayed with hue gradation according to an elastic value. At the same time, a region where no proper pressure is applied is displayed with no gradation such that an image can be identified by a single hue different from the hues of gradation.

With the display value evaluating section 215 and the color scan converter 213 of the present embodiment, it is possible to stably perform high-quality and reliable elastic imaging without being mislead by information on an insignificant elastic image region having not been removed, and simultaneously it is possible to feed back causes including an improper operating method (pressing method, etc.) and device setting to the operator through an elastic image, thereby instantly providing an operating method (pressing method, etc.) enabling a higher quality image at the site of imaging.

According to the present embodiment, in the display value evaluating section 215, decision result frame data is generated in which a measuring point worth displaying is set at "0" and a measuring point not worth displaying is set at "1". Additionally, of all the elements (N×M) of decision result frame data, a ratio R of measuring points where the elements of decision result frame data are "1" may be determined by an operation below:

(ratio $R$)=[$\Sigma$ {(decision result frame data $Z_{i,j}$)= 1}]/($N \times M$)

When the determined ratio R is smaller than a reference ratio Rstd (e.g., 0.5), it is decided that just a few measuring points are worth displaying in a frame, and decision result frame data is generated again by resetting all the element data of the decision result frame data at "0" as follows:

(ratio $R$)<(reference ratio $R$std) $\Rightarrow$(decision result frame data $Z_{i,j}$)=0

($i$=1, 2, 3, ..., N, $j$=1, 2, 3, ..., M)

Figure 29:
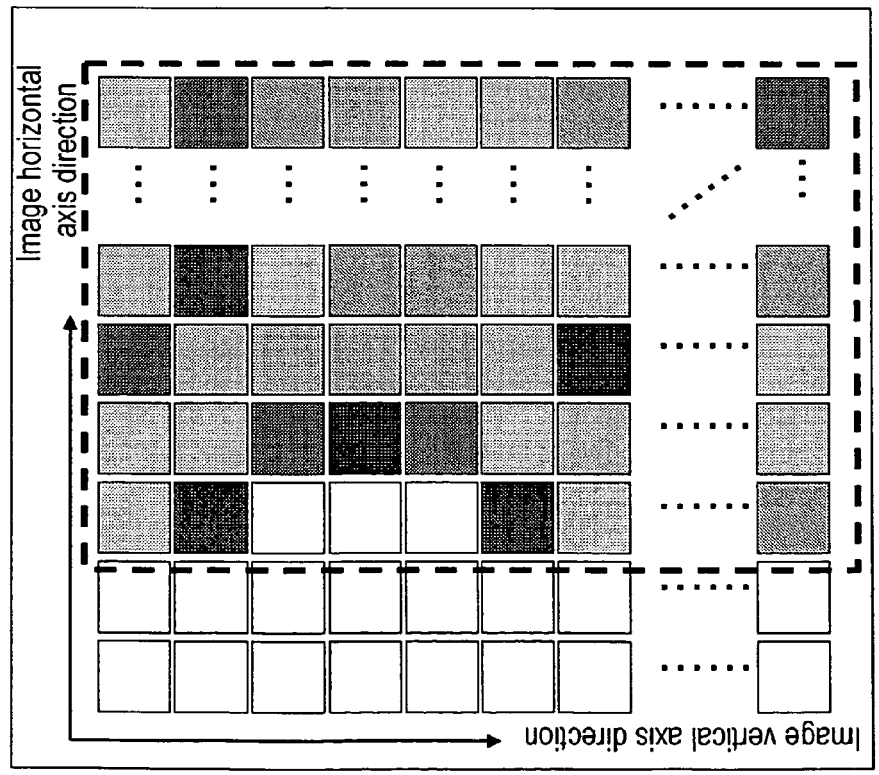
FIG. 29 is a diagram showing an example of elastic hue frame data in which all element data is constructed with the same single color and the elastic image data of a frame is displayed without gradation processing.

With this operation, in elastic gradation frame data $T_{i,j}$ generated by the color scan converter 213, all element data $T_{i,j}$ are set at "0" according to the decision result frame data $Z_{i,j}$. Thus, in elastic hue frame data $U_{ci,j}$, for example, all element data are constructed with the same single color as shown in FIG. 29, and the elastic image data of a frame is displayed with no gradation. That is, elastic image data is not displayed. Hence, elastic image data is not displayed in the fifth aspect where a region of interest is a region in which the ultrasound probe is not in contact with the subject, and additionally in an aspect where the operator searches for an affected part while moving an ultrasound probe head in contact with the subject along a body side.

In the foregoing embodiment, the display value evaluating section 215 evaluates variations of elements within a local kernel size of displacement frame data or elastic frame data serve as a population. Decision result frame data is generated in which a measuring point worth displaying is set at "0" and a measuring point not worth displaying is set at "1". Different processing may be performed as follows: statistical processing is performed in which all the elements of the element data $X_{i,j}$ of measurement result frame data serve as a population, and an average M serving as a statistical characteristic amount is determined by an operation below:

(average value $M$)={$\Sigma$(measurement result frame data $X_{i,j}$)}/($N \times M$)

($i$=1, 2, 3, ..., N, $j$=1, 2, 3, ..., M)

When the average M is smaller than a reference average Mstd, it is decided that just a few measuring points are worth displaying in a frame, and decision result frame data is generated again by resetting all the element data of the decision result frame data at "0" as follows:

(average $M$)<(reference average $M$std) $\Rightarrow$(decision result frame data $Z_{i,j}$)=0

($i$=1, 2, 3, ..., N, $j$=1, 2, 3, ..., M)

With this operation, in elastic gradation frame data $T_{i,j}$ generated by the color scan converter 213, all element data $T_{i,j}$ are set at "0" according to decision result frame data $Z_{i,j}$. Thus, in elastic hue frame data $U_{i,j}$, for example, all element data are constructed with the same single color as shown in FIG. 29, and the elastic image data of a frame is displayed with no gradation.

In the foregoing embodiment, the display value evaluating section 215 makes evaluations in which the elements of displacement frame data, that is, elastic frame data serve as a population. Decision result frame data is generated in which a measuring point worth displaying is set at "0" and a measuring point not worth displaying is set at "1". Different processing may be performed as follows:

Pressure data P outputted from the pressure measuring section 210 is inputted as measurement result frame data. When the pressure P is smaller than a reference ratio Pstd, it is decided that just a few measuring points are worth displaying in a frame, and decision result frame data is generated again by resetting all the element data of the decision result frame data at "0" as follows:

(pressure $P$)<(reference pressure $P$std) $\Rightarrow$(decision result frame data $Z_{i,j}$)=0

($i$=1, 2, 3, ..., N, $j$=1, 2, 3, ..., M)

With this operation, in elastic gradation frame data $T_{i,j}$ generated by the color scan converter 213, all element data $T_{i,j}$ are set at "0" according to decision result frame data $Z_{i,j}$. Thus, in elastic hue frame data $U_{i,j}$, for example, all element data are constructed with the same single color as shown in FIG. 29, and the elastic image data of a frame is displayed with no gradation.

When the pressure data P is obtained as Pi ($i$=1, 2, 3, ..., N) in a one-dimensional distribution of the horizontal axis direction of an image, the pressure data P is compared with a reference pressure Pstd according to coordinates i. On coordinates not satisfying the reference pressure Pstd, decision result frame data $Z_{i,j}$ of the corresponding coordinates is set at "0".

At the site of actual imaging, a region having a displacement close to 0 is entirely distributed in ROI set by the imaging apparatus due to a pressing speed of 0 or an insufficient pressing speed, for example, in a sixth aspect where a pressure is not applied to a tissue of interest during a time interval when a pair of ultrasound received signal frame data is obtained, and a seventh aspect where a pressing speed on a tissue of interest is too low. To be specific, the operator searches for an affected part while moving the ultrasound probe head in contact with the subject along a body side. Such a case corresponds to these aspects. In the sixth and seventh aspects, a region having a displacement close to 0 is distributed over a region set as a region of interest (ROI). Thus, a distortion image displayed with a distortion calculated using the displacement is an image with no contrast or a low contrast over the set ROI. In aspects represented by the sixth and seventh aspects, first and second frames discussed below are observed as a result of a tissue displacement made by a pressure.

A first frame is a frame where measuring points are not entirely displaced and no pressure is applied (an average of displacements or elastic values is 0) and a second frame is a frame where measuring points are entirely displaced just a little and only a low pressure is applied (an average of displacements or elastic values is small). The two first and second broadly divided frames may be observed in a plurality of elastic image frames in a series of pressing processes.

The foregoing embodiment described that displacement frame data or elastic frame data is used in the display value evaluating section 215 and the color scan converter 213. In this operation, an average of displacements or elastic values is determined. The overall elements of displacement frame data or elastic frame data serve as a population. A frame with an average determined to be lower than a predetermined reference value is entirely evaluated as being less worth displaying. When an overall frame is decided to be less worth displaying, all the elastic image information of the frame is removed and elastic images where a single hue is added with no gradation are collectively displayed on the screen of the ultrasound imaging apparatus. Only for a frame in a times phase when a proper pressure is applied, an elastic image is displayed with levels of hues corresponding to the elastic values. Gradation is removed from a frame in a time phase when a proper pressure is not applied, and an image is displayed with a single hue different from hues of gradation, so that it is possible to recognize a frame in a time phase when a proper pressure is not applied.

In the elasticity imaging method of the ultrasound imaging apparatus, an image is constructed and displayed for each frame in a given time phase without evaluating whether an elastic value (a distortion or modulus of elasticity) outputted as an arithmetic result is worth displaying or not (evaluating image quality). Thus, at the site of actual imaging, even though image information calculated under improper conditions is a frame not worth displaying, the frame is not differentiated from a frame worth displaying, an elastic image of a series of consecutive frames is constructed such that frames of both types are mixed. Consequently, the reliability of elasticity imaging decreases. In contrast, according to the present invention, it is possible to stably perform high-quality and reliable elastic imaging without being mislead by information on an insignificant elastic image frame having not been removed, and simultaneously it is possible to feed back causes including an improper operating method (pressing method, etc.) to the operator through an elastic image, thereby instantly searching for a pressing method or the like enabling a higher quality image at the site of imaging.

Moreover, in a configuration where a color elastic image is translucently superimposed and displayed on a monochrome tomographic image, according to the present invention, an elastic image is superimposed and displayed only during a pressing operation. In a time phase when a pressure is stopped, for example, the operator brings the ultrasound probe head into contact with the subject and searches for an affected part while moving the ultrasound probe head in contact with the subject along a body side, elastic images are removed and thus only monochrome tomographic images are transmitted and displayed. Hence, it is possible to easily confirm a tomographic image on a measuring cross section in a time phase other than elasticity imaging, thereby considerably improving efficiency of interpretation.

In the foregoing embodiment, region removal (region removing function) in one frame and removal over one frame (frame removing function) were separately described in detail. The present invention is not limited to these operations. The two operations may be combined and performed at the same time, and a configuration for the combined operations may be provided.

The foregoing embodiment described that when the removal of a frame is decided by the frame removal function according to an evaluation at the current time, the image information on the frame at the current time is set at a single hue and displayed. The present invention is not limited to this example. When the removal of a frame is decided at the current time, the closest past frame displayed without being removed may be kept and continuously displayed. This operation is not limited to the frame removal function. The same function may be set for the operation of the region removal function.

The foregoing embodiment described the display value evaluating section 215 as an independent circuit. The present invention is not limited to this configuration. The operation of the display value evaluating section 215 may be included in the color scan converter 213 or the elastic data processing section 212, or the order of processing circuits may be changed.

In the present embodiment, the operator can freely control, via the device control interface 216 included in the ultrasound apparatus, the selection of the region removal function and the frame removal function, the settings of a threshold value for threshold processing in the removal function, a reference ratio, a reference average or the like, and the allocation and switching of hues added to a removed region and a removed frame.

According to the present embodiment, even when ideal data is hard to obtain in elasticity imaging, a region of image information including an elastic value not worth displaying is recognized (as noise), an overall frame is recognized (as noise) when elastic values not worth displaying are calculated over the frame, and an elastic image reflecting the information is constructed, thereby providing an ultrasound imaging apparatus enabling high-quality elasticity imaging.

The following will describe the operations of the ultrasound imaging apparatus configured thus. First, according to ultrasound wave transmission/reception control, a high-voltage electrical pulse is applied from the transmitter circuit 202 to the ultrasound probe 10 in contact with the subject 1, an ultrasound wave is emitted, and a reflected echo signal from an imaging target is received by the ultrasound probe 10. The received signal is inputted to the receiver circuit 203 and preamplified therein. After that, the received signal is inputted to the phasing/adding circuit 204. To evaluate elasticity of a part of interest in a tissue of the subject by using the ultrasound probe 10 comprising the automatic pressing mechanism 20, the ultrasound probe 10 is brought into contact with the subject 1 while pressing the subject 1 according to a proper pressing method automatically set by the automatic pressing mechanism 20, so that consecutive ultrasound received signal frame data are outputted from the phasing/adding circuit 204.

Received signals aligned in phase in the phasing/adding circuit 204 undergo signal processing such as compression and detection in the subsequent signal processing section 205, and then the signals are inputted to the monochrome scan converter 206. The monochrome scan converter 206 AD converts the received signals and stores the signals as a plurality of time-series consecutive tomographic image data in a plurality of frame memory in the monochrome scan converter 206. Ultrasound received signal frame data is successively outputted from the phasing/adding circuit 204 and inputted to the ultrasound received signal frame data selecting section 208.

Of the ultrasound received signal frame data stored in the ultrasound received signal frame data selecting section 208, a plurality of time-series consecutive ultrasound received signal frame data are selected, inputted to the displacement measuring section 209, and a one-dimensional or two-dimensional displacement distribution ($\Delta L_{i,j}$) is determined. The displacement distribution is calculated by using, for example, a block matching method as the method of detecting a movement vector. The method is not particularly limited. As in a generally used method, a displacement may be calculated by calculating autocorrelation of two image data in the same region.

Period information between a pair of ultrasound received signal frame data selected by the ultrasound received signal frame data selecting section 208 is outputted to the automatic pressing mechanism 20, and the pressing operation of the automatic pressing mechanism 20 is optimized according to the period information. In the pressure measuring section 210, a pressure applied to the subject 1 is measured, pressure information is transmitted from the pressure measuring section 210 to the distortion/elasticity modulus calculating section 211 and the automatic pressing mechanism 20, and the pressing operation of the automatic pressing mechanism 20 is optically controlled according to the pressure information, so that elastic imaging can be efficiently performed on the subject.

The measurement signals of a displacement ($\Delta L_{i,j}$) and a pressure ($\Delta P_{i,j}$) outputted from the displacement measuring section 209 and the pressure measuring section 210 are inputted to the distortion/elasticity modulus calculating section 211. A distortion distribution ($\epsilon_{i,j}$) is calculated by spatial differentiation ($\Delta L_{i,j}/\Delta X$) on a displacement distribution ($\Delta L_{i,j}$). Particularly, of modulus of elasticities, a Young's modulus $Ym_{i,j}$ is calculated by the formula below:

$$Ym_{i,j}=(\Delta P_{i,j})/(\Delta L_{i,j}/\Delta X)$$

A modulus of elasticity on each measuring point is obtained by the modulus of elasticity $Ym_{i,j}$ determined thus, and elastic frame data is generated.

The elastic frame data generated thus is inputted to the elastic data processing section 212 and undergoes various kinds of image processing such as smoothing in a coordinate plane, contrast optimization, and smoothing in the time-axis direction between frames.

The display value evaluating section 215 is fed with displacement frame data outputted from the displacement measuring section 209 or elastic frame data outputted from the distortion/elasticity modulus calculating section 211, evaluates whether an elastic image is worth displaying or not on each measuring point or frame, generates evaluation result frame data according to the evaluation, and outputs the evaluation result frame data to the color scan converter 213 or the monochrome scan converter 206.

The elastic frame data outputted from the elastic data processing section 212 and the evaluation result frame data outputted from the display value evaluating section 215 are inputted to the color scan converter 213 or the monochrome scan converter 206. According to information on the evaluation result frame data, removal is performed on useless elastic information, and simultaneously useful information is converted to hue information, which has undergone gradation processing, or monochrome brightness information.

Thereafter, a monochrome tomographic image and a color elastic image are added and combined through the switching adder 214, or a monochrome tomographic image and a color elastic image are sent to the image display 207 without additions. A monochrome tomographic image and a color elastic image, which have undergone translucent processing, are superimposed and displayed on one screen, or a monochrome tomographic image and a color elastic image are simultaneously displayed on the same screen. The monochrome tomographic image is not particularly limited to an ordinary B-mode image. A tissue harmonic tomographic image formed by selecting harmonic components of a received signal may be used. A tissue Doppler image may be similarly displayed instead of a monochrome tomographic image. Additionally, images displayed on two screens may be selected in various combinations.

The foregoing formation of an elastic image is an example where the distortion or Young's modulus Ym of a living tissue is determined to generate elastic image data. The present invention is not limited to these parameters. For example, a modulus of elasticity may be calculated using other parameters including a stiffness parameter β, a pressure elastic modulus Ep, an incremental elastic modulus Einc (e.g., Japanese Patent Application Laid-Open No. 5-317313).

With this configuration, even when ideal data is hard to obtain in elasticity imaging performed by the ultrasound imaging apparatus of the present invention, a region of image information including a value of elasticity not worth displaying is recognized as noise, an overall frame is recognized as noise when values of elasticity not worth displaying are calculated over the frame, and an elastic image reflecting the information is constructed, thereby providing an ultrasound imaging apparatus enabling high-quality elasticity imaging.

An elastic image may be kept without being rejected. The foregoing embodiment described that when the removal of a frame is decided by the frame removal function according to an evaluation of display value at the current time, the image information of the frame at the current time is set at a single hue and displayed. The present invention is not limited to this example. When the removal of a frame is decided at the current time, the closest past frame displayed without being removed may be kept and continuously displayed. This operation is not limited to the frame removal function. The same function may be set for the operation of the region removal function.

Figure 30:
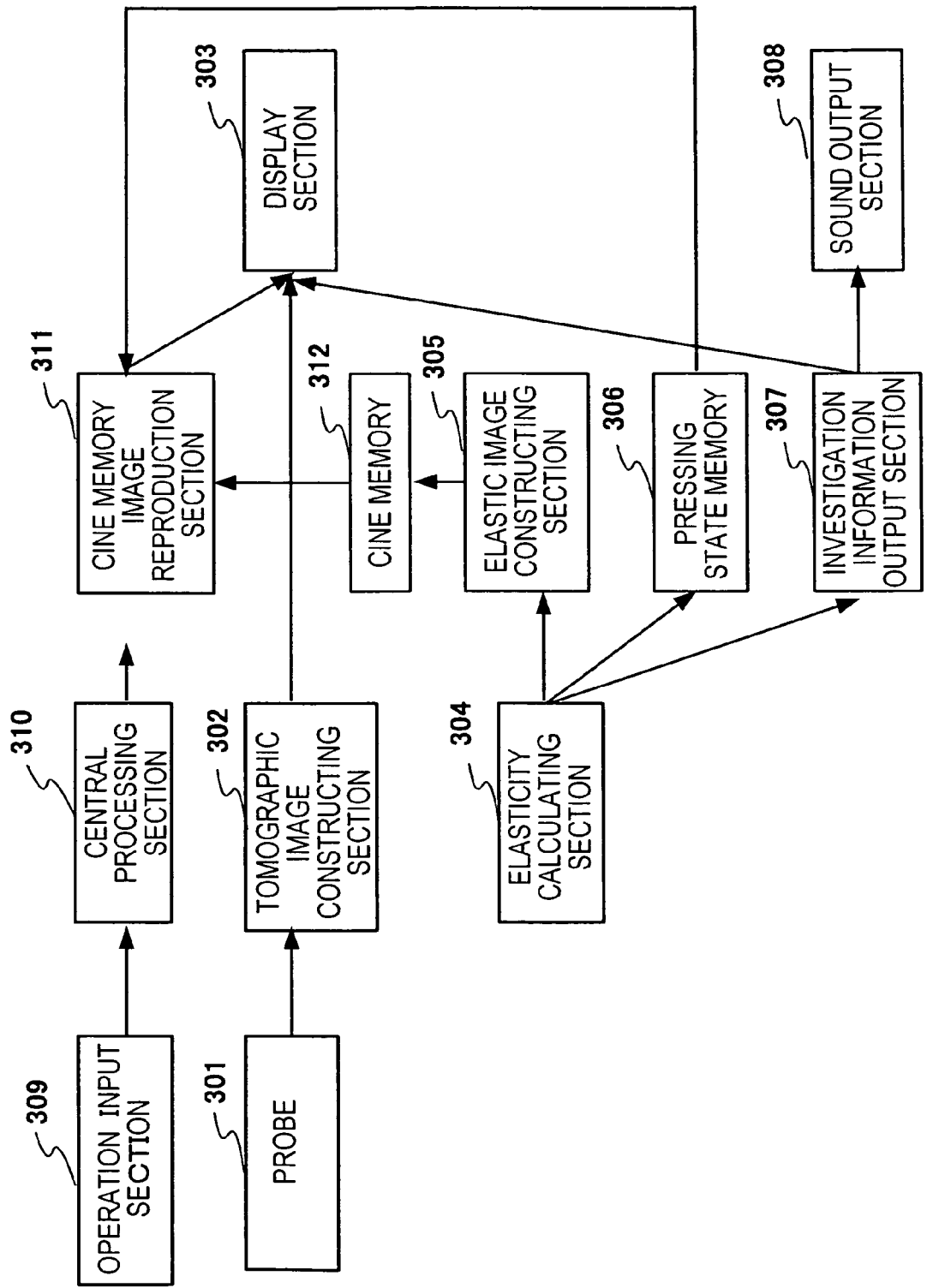
FIG. 30 is a block diagram showing the configuration of another embodiment of an ultrasound imaging apparatus according to the present invention.
Figure 31:
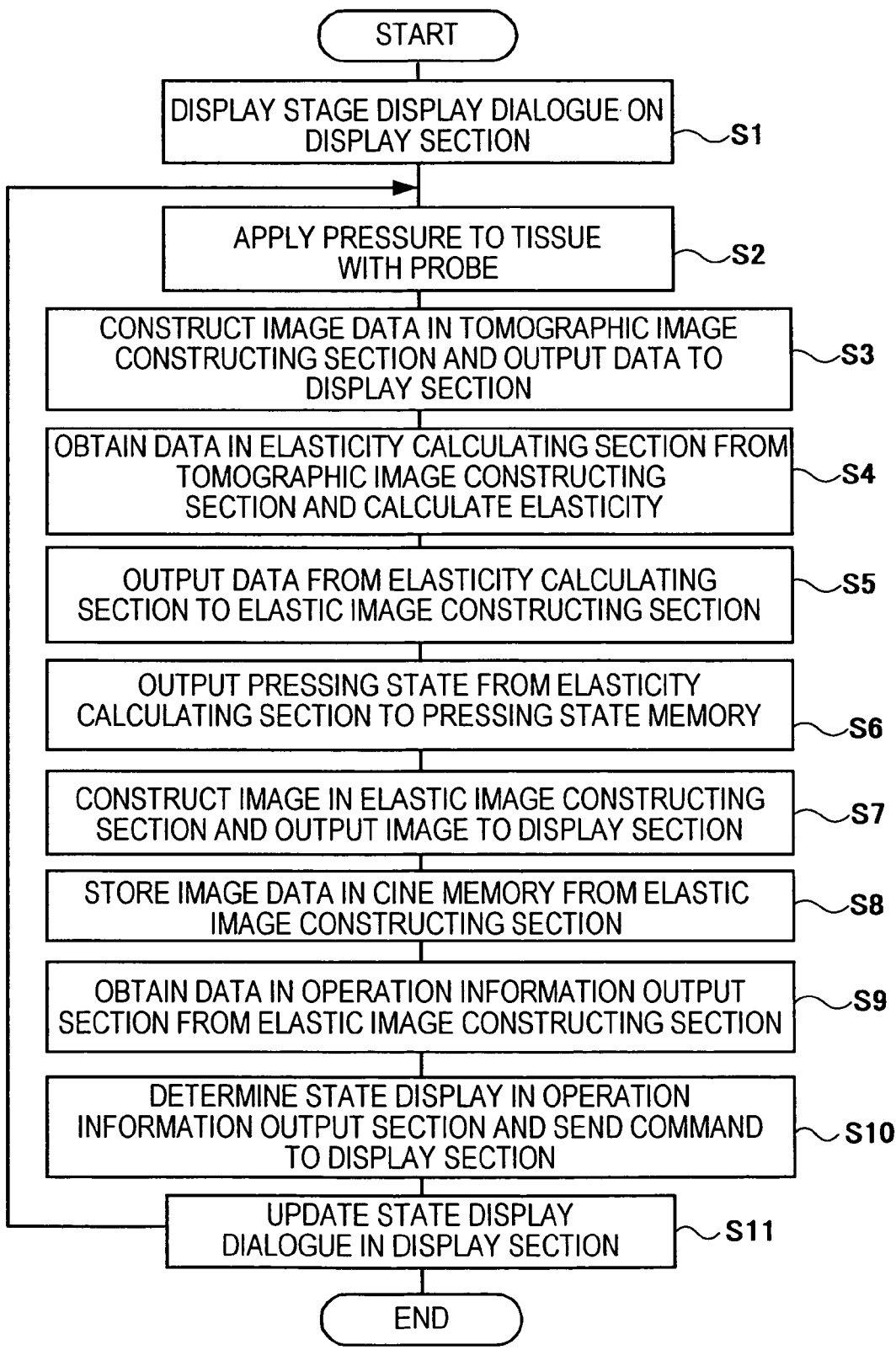
FIG. 31 is a flowchart showing the steps of obtaining an elastic image in the ultrasound imaging apparatus of the embodiment shown in FIG. 30.

Another embodiment of the present invention will be described below. FIG. 30 is a block structural diagram showing an ultrasound imaging apparatus of the present embodiment. FIG. 31 is a flowchart showing the steps of obtaining an elastic image in the ultrasound imaging apparatus of the present embodiment. FIGS. 32(a) to 32(e) are diagrams showing an example of displayed images of the present embodiment.

As shown in FIG. 30, the ultrasound imaging apparatus of the present embodiment comprises a probe 301 for transmitting and receiving ultrasound waves to and from a subject, a tomographic image constructing section 302 which captures a reflected echo signal outputted from the probe 301 and reconstructs a tomographic image, and a display section 303 for displaying the reconstructed tomographic image. Ultrasound wave transmitting device for outputting an ultrasound signal for driving the probe 301 is not illustrated. An elasticity calculating section 304 includes displacement measuring device which sequentially captures the frame data of reflected echo signals inputted to the tomographic image constructing section 302 and measures a displacement of a tissue in each part of a tomographic image based on two tomographic image data adjacent to each other in time series, and elastic modulus calculating device for calculating a modulus of elasticity of a tissue of each part based on displacement data of each part. The displacement data is measured by the displacement measuring device. The elasticity calculating section 304 comprises pressing decision device for analyzing displacement data to decide whether a pressing operation is proper or not.

An elastic image constructing section 305 generates an elastic image based on the modulus of elasticity determined by the elasticity calculating section 304, outputs the generated elastic image to the display section 303, and stores the elastic image in cine memory 312. The decision results of a pressing operation decided by the elasticity calculating section 304 are matched with respective elastic images, stored in pressing state memory 306, and outputted to an operation information output section 307. The operation information output section 307 outputs the decision result of a pressing operation to the display section 303 and displays the results. The operation information output section 307 can output the decision result of a pressing operation as sound through a sound output section 308.

Various operation commands and setting information inputted from an operation input section 309 are inputted to a central processing section 310, and the central processing section 310 controls a cine memory image reproduction section 311 and so on in response to an inputted command or the like.

Figure 32:
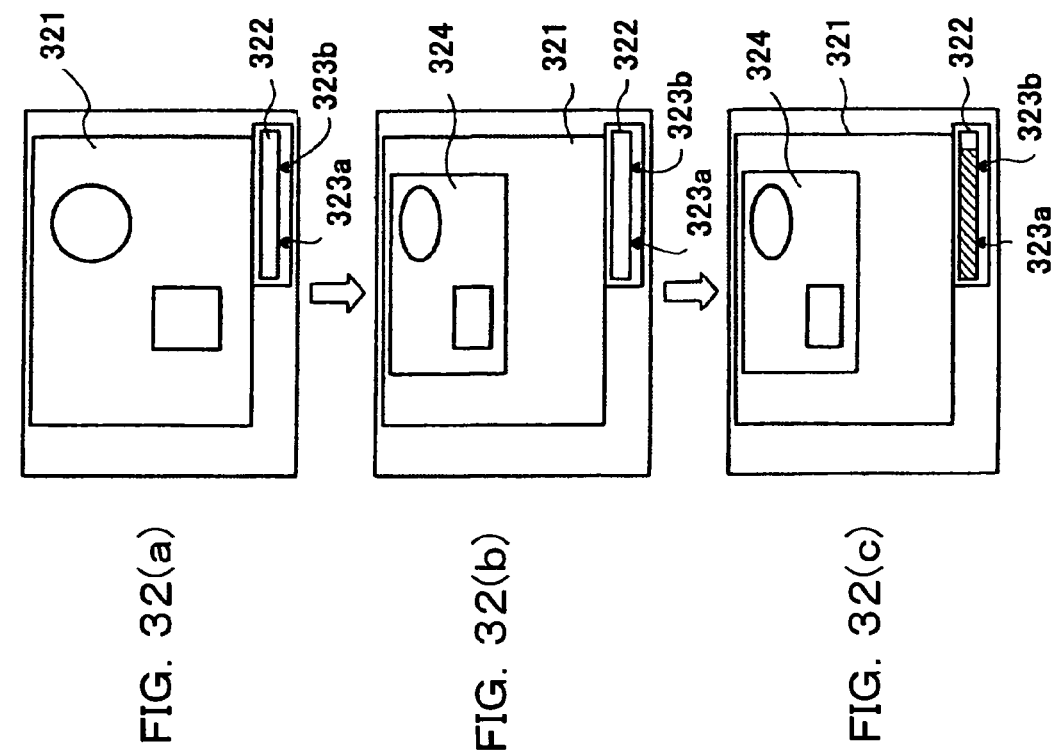
FIGS. 32(a) to 32(e) are diagrams showing an example of displayed images according to the embodiment of FIG. 31.

Referring to the flowchart of FIG. 31 and examples of displayed images of FIGS. 32(a) to 32(e), the following will describe an operation of obtaining an elastic image in the ultrasound imaging apparatus configured thus. First, as shown in FIG. 32(a), at the start of a measurement of an elastic image, a tomographic image 321 is outputted from the tomographic image constructing section 302 to the display section 303 to display the tomographic image, and a dialog 322 for indicating a pressing state is displayed from the operation information output section 307 to the display section 303 (S1). The dialog 322 has a horizontally oriented display region like a bar chart. Two triangle marks 323a and 323b are displayed along the display region. The mark 323a corresponds to the lower limit value of a proper range of a pressing operation and the mark 323b corresponds to the upper limit value of the range.

Figure 33:
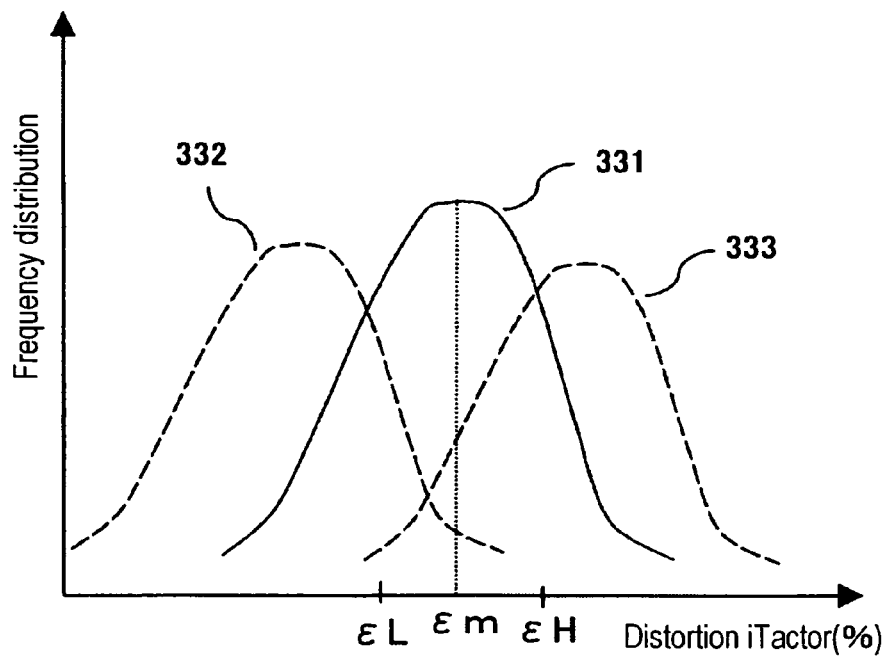
FIG. 33 is a diagram showing an example of a distortion factor distribution used for deciding whether a pressing operation is proper or not.

Then, the operator applies a pressure to the body surface of the subject with the probe 301 to apply a pressure to a living tissue (S2). In this pressing state, the tomographic image constructing section 302 successively captures reflected echo signals and updates the tomographic image of the display section 303 (S3). The elasticity calculating section 304 sequentially obtains frame data of a tomographic image from the tomographic image constructing section 302, measures a displacement of a tissue of each part based on two frame data adjacent to each other in time series, calculates a modulus of elasticity of a tissue of each part based on measured displacement data of each part (S4), and outputs data on the calculated modulus of elasticity to the elastic image constructing section 305 (S5). In step S4, the elasticity calculating section 304 analyzes displacement data to decide whether a pressing operation is proper or not, and outputs the pressing state of a decision result to the pressing state memory 306 (S7). In this decision, for example, as shown in FIG. 33, a distribution 331 of distortion factors $\epsilon$ in a tomographic image is determined based on displacement data, that is, the distribution of the distortion factors $\epsilon$ is determined with a horizontal axis representing a distortion factor of each pixel and a vertical axis representing the number of pixels having a uniform distortion factor. It is decided whether a pressing operation of pressing device is proper or not depending on whether an average $\epsilon m$ of the distortion factor distribution 331 is within the range of the upper and lower limit values ($\epsilon H$, $\epsilon L$) of the proper range. For example, in FIG. 33, distortion factor distributions 332 and 333 indicated by broken lines are improper examples because averages are placed out of the upper and lower limit values ($\epsilon H$, $\epsilon L$). The distortion factor distribution 332 is an example of a slow pressing speed. The distortion factor distribution 333 is an example of a fast pressing speed. For example, a pressing state is judged according to eight evaluation levels, stored in the pressing state memory 306, and outputted to the operation information output section 307.

The elastic image constructing section 305 constructs an elastic image by color mapping based on elasticity modulus data outputted from the elasticity calculating section 304, and displays an elastic image 324 superimposed on the tomographic image 321 of the display section 303 as shown FIG. 32(b) (S7). The elastic image data is stored in the cine memory 312 (S8). Subsequently, the operation information output section 307 obtains the evaluation level of a pressing state outputted from the elasticity calculating section 304 (S9), determines display of a state of the dialog 322 according to the level, and outputs the indication of a state to the display section 303 (S10). For example, as shown in FIG. 32(c), the display section 303 updates the indication of the dialog 322. FIG. 32(c) shows an example in which the evaluation level of a pressing state exceeds the proper range. In response to the indication of the dialog 322, the operator reduces the pressing speed, thereby obtaining a proper elastic image of FIG. 32(d) according to the adjusted pressing speed during the subsequent elastic image formation performed back in step S2 of FIG. 31. Therefore, as shown in FIG. 32(e), the indication of the state of the dialog 322 is within the proper range of the marks 323a and 323b, indicating that a proper elastic image is obtained. In FIGS. 32(a) to 32(e), the marks 323a and 323b of the dialog 322 correspond to the upper and lower limit values ($\epsilon H$, $\epsilon L$) of the proper range.

In this way, according to the present embodiment, the dialog 322 immediately indicates whether a pressing operation is proper or not. The operator adjusts the operation of the probe 301 depending upon whether a pressing state indicated by the dialog 322 is proper or not, thereby readily performing a pressing operation for obtaining a proper elastic image. In addition, the present embodiment makes it possible to decide whether a pressing operation is proper or not in consideration of variations among subjects, and thus the operator can perform a proper pressing operation with great ease.

Figure 34:
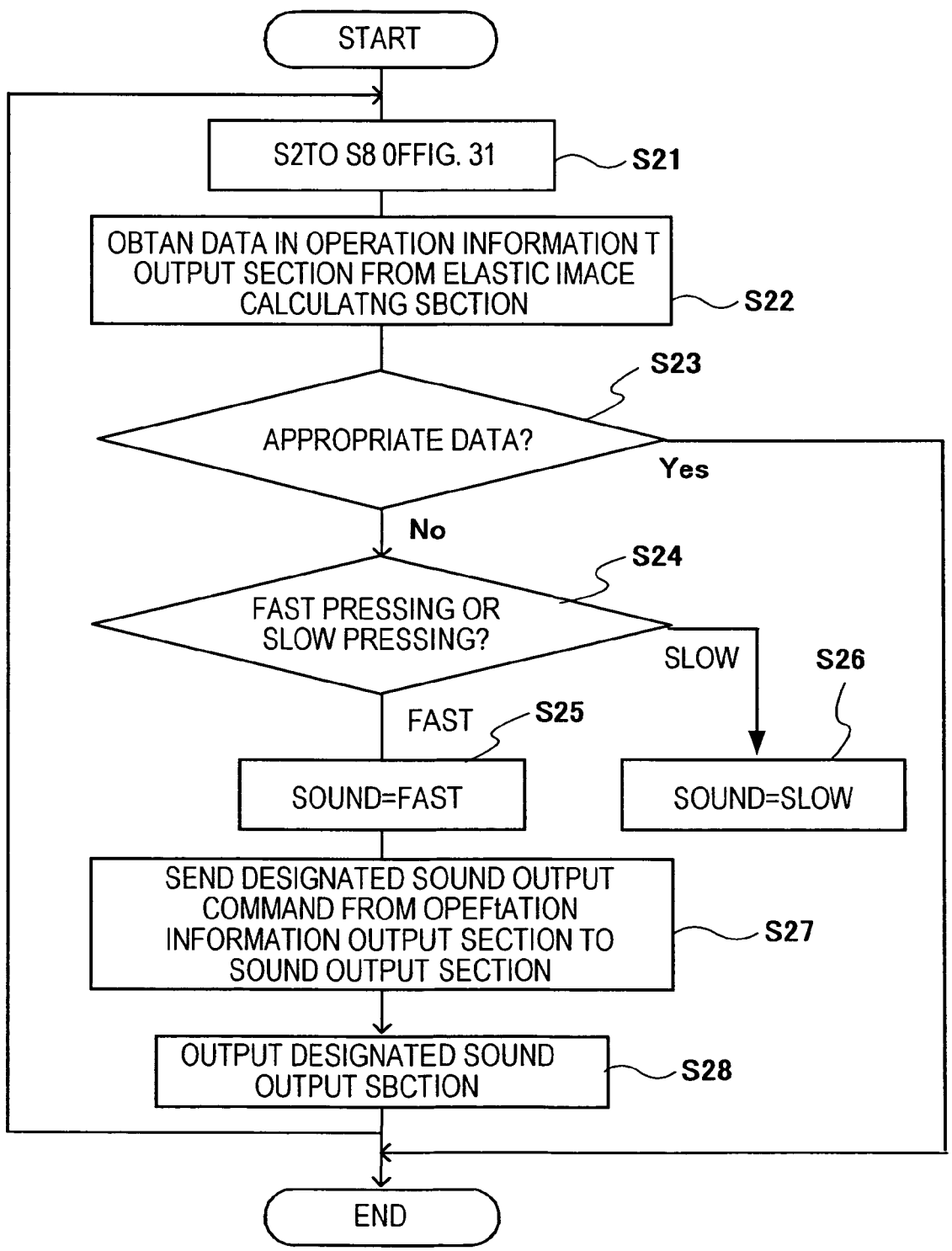
FIG. 34 is a flowchart for outputting as sound whether a pressing operation is proper or not.
Figure 35A:
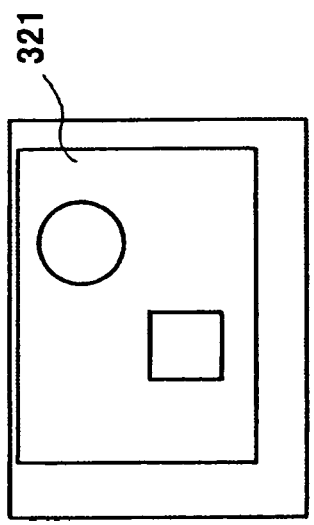
FIGS. 35(a) to 35(e) are diagrams showing an example of displayed images according to the embodiment of FIG. 34.
Figure 35B:
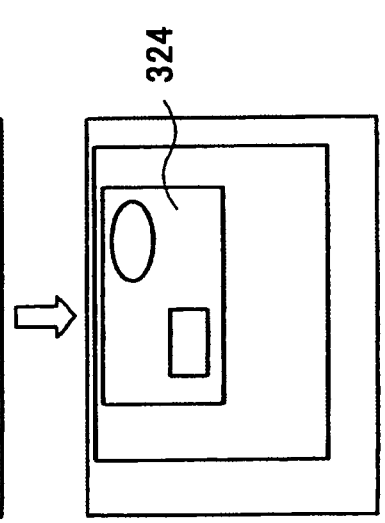
Figure 35C:
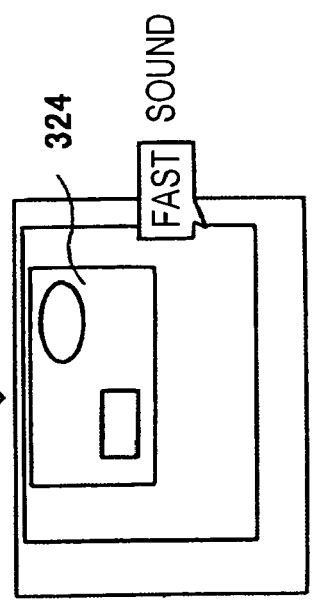
Figure 35D:
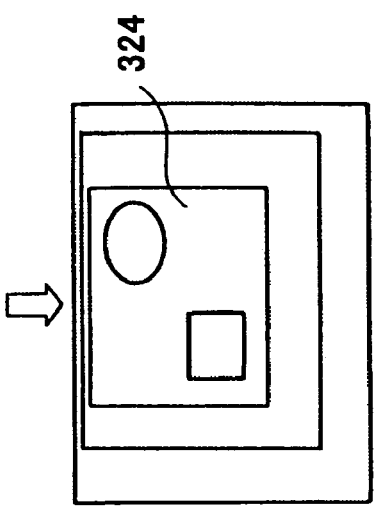
Figure 35E:
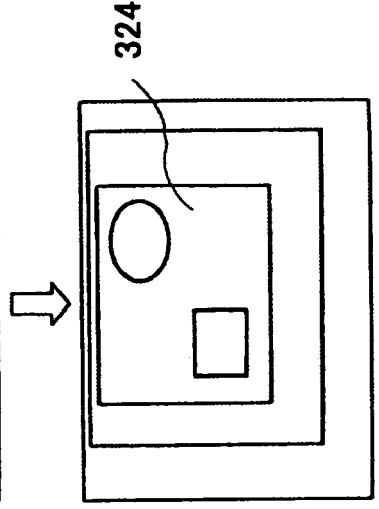

In the foregoing embodiment, the display section 303 displays whether a pressing operation is proper or not through the dialog. The present invention is not limited to this example. Whether a pressing operation is proper or not may be outputted as sound. FIG. 34 is a flowchart for outputting as sound whether a pressing operation is proper or not. FIGS. 35(a) to 35(e) show an example of displayed images in this case. In FIG. 34, step S21 is similar to steps S2 to S8 of FIG. 31. The operation information output section 307 obtains the evaluation level of a pressing state outputted from the elasticity calculating section 304 (S22) and decides whether the evaluation level is appropriate (proper) or not (S23). When the evaluation level is proper, processing is completed. When the evaluation level is not proper, it is decided whether the evaluation level is "fast" or "slow" out of the proper range, and an evaluation result is set at sound of "fast" or "slow" (S25, S26). Thus, a sound output command of "fast" or "slow" is outputted from the operation information output section 307 (S27), and an evaluation result, i.e., operation information is outputted as a sound designated by the sound output section 308. FIGS. 35(a) to 35(e) show an example of displayed images.

In this way, according to the present embodiment, the operator can obtain operation information through sound without viewing displayed images. Thus, it is possible to easily perform a pressing operation for obtaining a proper elastic image.

Figure 36:
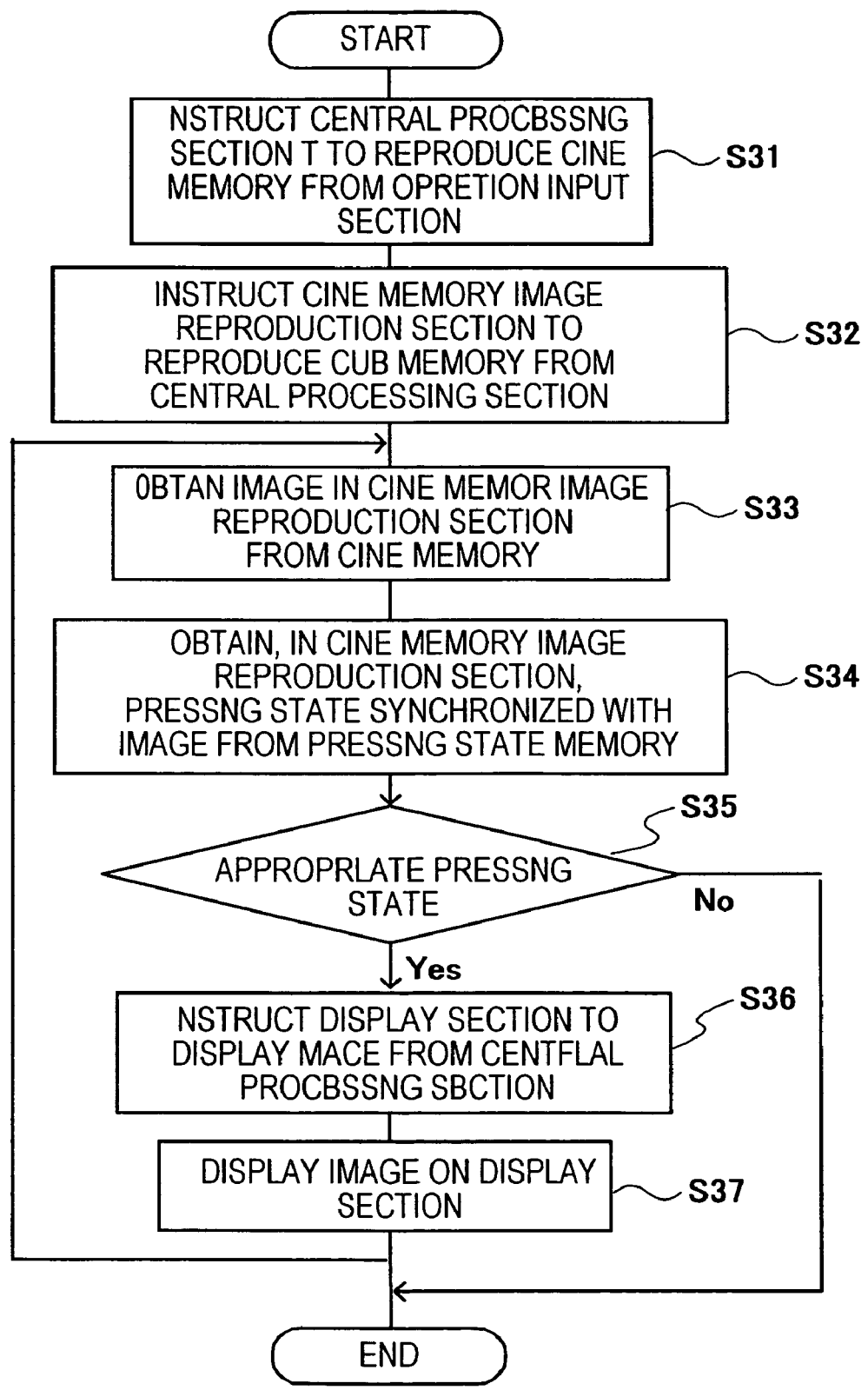
FIG. 36 is a flowchart showing that an elastic image stored in cine memory is reproduced and displayed.

FIG. 36 is a flowchart showing the reproduction and display of an elastic image stored in the cine memory 312 of FIG. 30. When the operation input section 309 instructs the CPU 310 to reproduce the cine memory (S31), the CPU 310 outputs a cine memory reproduction command to the cine memory image reproduction section 311 (S32). Hence, the cine memory image reproduction section 311 obtains an elastic image from the cine memory 312 (S33) and obtains the evaluation result of a pressing state in synchronization with an elastic image read from the pressing state memory 306 (S34). Then, it is decided whether the read pressing state is appropriate or not (S35). When the pressing state is not appropriate, the processing is completed. When the pressing state is appropriate, the CPU 310 outputs a command for instructing the display section 303 to display an elastic image reproduced by the cine memory image reproduction section 311 (S36). Thus, an elastic image stored in the cine memory 312 is displayed on the display section 303 (S37). That is, only a proper elastic image stored in the cine memory 312 is reproduced and displayed.

The present embodiment provides operation information on whether a pressing speed is proper or not. The present invention is not limited to this example. Operation information can be provided in the event of a pressing operation causing lateral displacement of a living tissue. In other words, even when a pressing speed is constant over time periods in a process of a pressing operation, the subject is not always pressed evenly in the vertical direction over the time periods (hereinafter, referred to as time phases). For example, in a time phase when the subject is pressed diagonally or unevenly, the stress distribution of a living tissue becomes discontinuous in some time phases. In such time phases, coordinate regions appear which are discontinuous relative to time changes. Thus, an obtained elastic image includes a temporally discontinuous region as disturbance (noise), so that elasticity imaging cannot be properly performed. In other words, when lateral displacement occurs, which is a lateral movement of a living tissue, due to an uneven pressure in the vertical direction, elasticity imaging cannot be properly performed.

Figure 37:
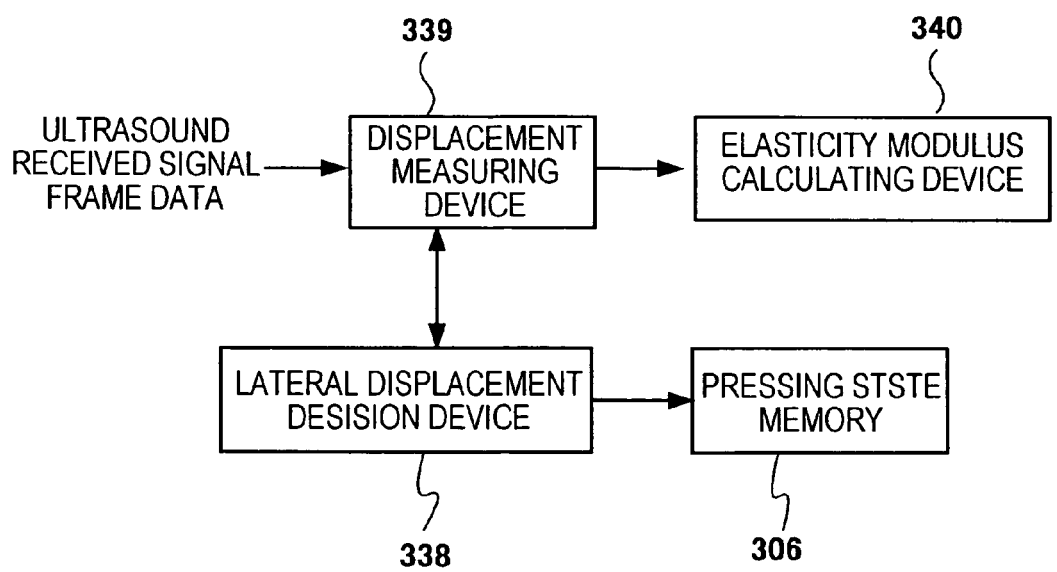
FIG. 37 is a block diagram showing a configuration around lateral displacement decision device according to the embodiment of the present invention.

In the present embodiment, when a pressing operation causes lateral displacement of a living tissue, the lateral displacement is detected and operation information is provided. The present embodiment can be achieved by replacing the pressing decision device constituting the elasticity calculating section 304 in the embodiment of FIG. 30 with lateral displacement decision device 338. In other words, as shown in FIG. 37, from displacement measuring device 339 for capturing frame data of ultrasound received signal data from the tomographic image constructing section 302 and measuring a displacement, displacement data is captured to decide a degree of lateral displacement and a decision result is stored in the pressing state memory 306. In FIG. 37, elasticity modulus calculating device 340 calculates a modulus of elasticity of each part of a tissue based on displacement data and is a function included in the elasticity calculating section 304 of FIG. 30.

Figure 38:
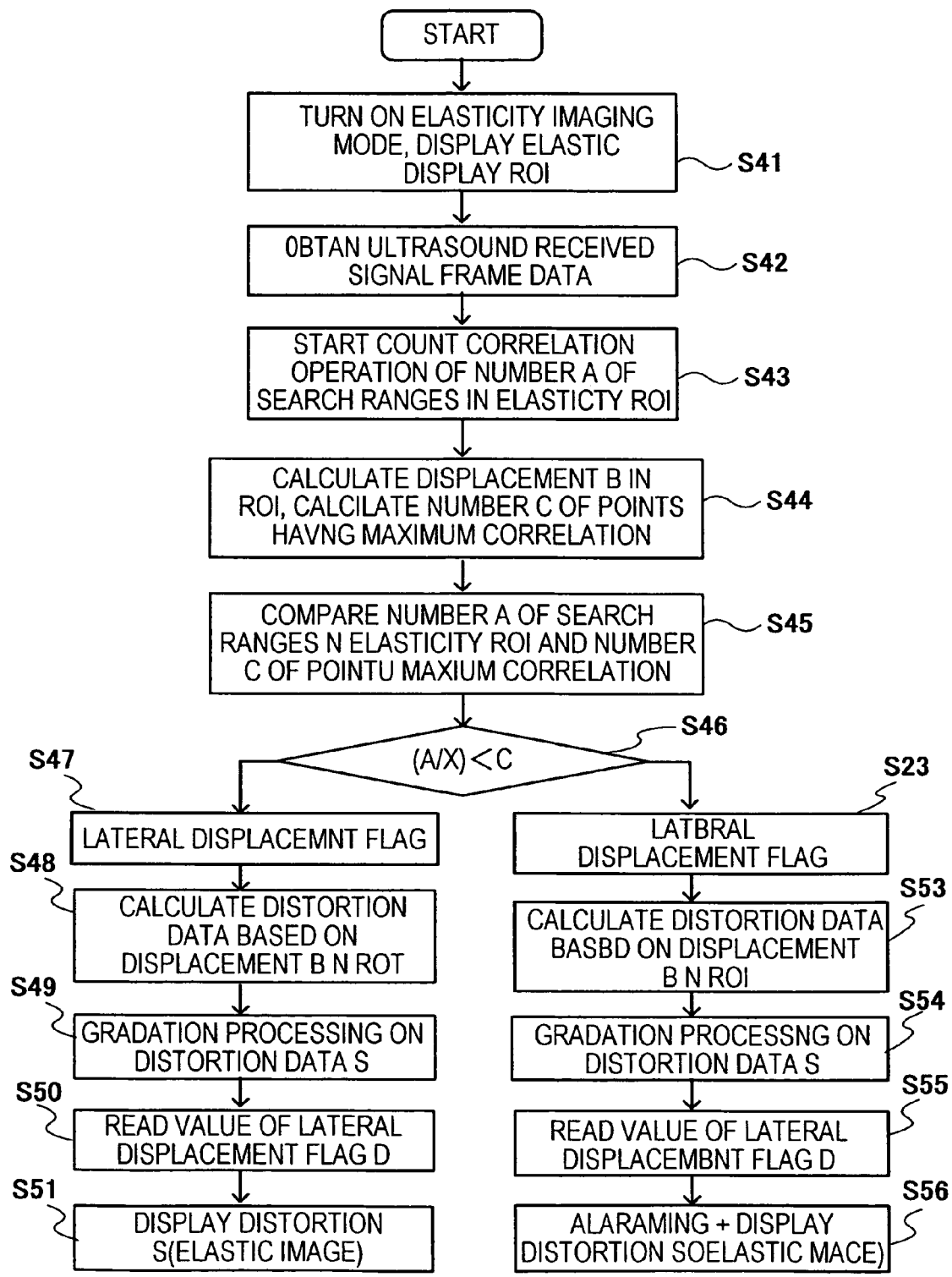
FIG. 38 is a flowchart mainly showing the steps in the lateral displacement decision device.
Figure 39:
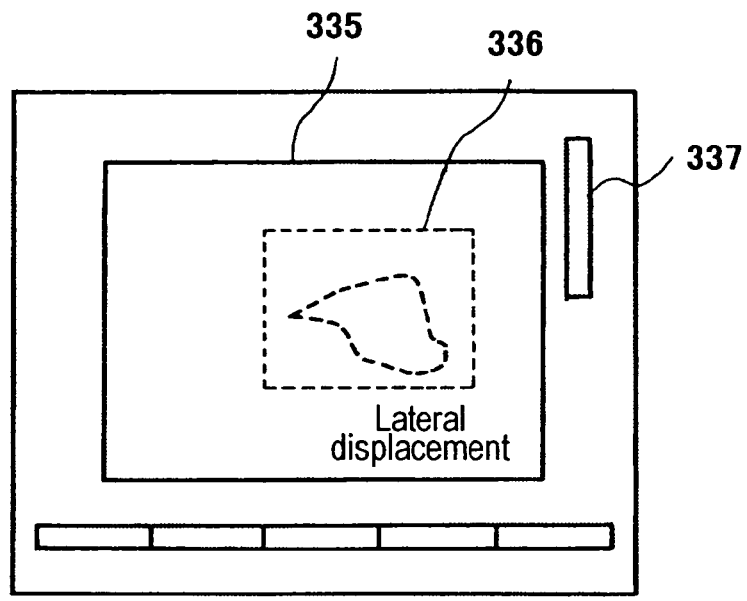
FIG. 39 is a diagram showing a state of a displayed image according to the embodiment of FIG. 37.

FIG. 38 is a flowchart mainly showing steps in the lateral displacement decision device 338 of the present embodiment. When an elasticity imaging mode is turned on from the operation input section 309 to the central processing section 310, as shown in FIG. 39, the display section 303 displays an ROI 336 for determining an elastic image for a tomographic image 335, and a color map 337 indicating a modulus of elasticity (S41). Then, the displacement measuring device 339 captures from the tomographic image constructing section 302 a pair of frame data adjacent to each other in time series (S42), measures a displacement or a movement vector (direction and size of a displacement) of each pixel on the tomographic image through correlation processing and so on, and detects a lateral displacement (S43 to S45).

Figure 40:
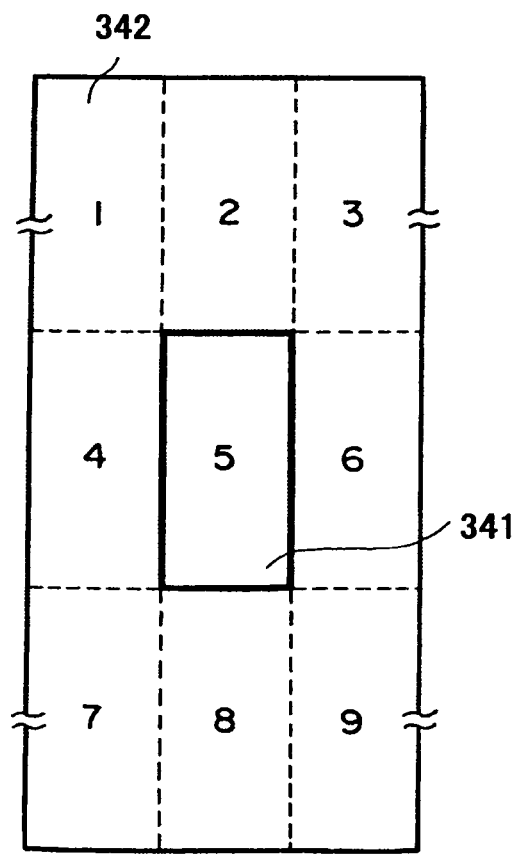
FIG. 40 is a diagram for explaining a block matching method for detecting lateral displacement.

For example, a well-known block matching method is applicable to correlation processing in the displacement measuring device 339. In the block matching method, an image is divided into blocks of N×N pixels (N is a natural number), the previous frame is searched for a block most approximate to a block of interest in the current frame, and predictive coding is performed with reference to the block. As shown in FIG. 40, a block composed of N×N pixels is a correlation window 341 and a region including a plurality of blocks of N×N pixels is a search range 342. The block having been referred in the previous frame is a point most correlated to the block of the current frame. For simple explanation, the search range 342 has a size of nine correlation windows 341 as shown in FIG. 40. To be specific, blocks identical in size to the correlation window 341 are arranged around the correlation window 341 in the horizontal and vertical directions and the diagonal directions. The correlation window 341 and the search range 342 can be set at random. Assuming that a stress from the probe is evenly applied to the subject in the vertical direction, the current frame and the previous frame are most correlated on blocks 2 and 8 disposed on and under the correlation window 341 at the center of FIG. 40. When a stress from the probe laterally moves a tissue of the subject, blocks 4 and 6 disposed on both sides of the correlation window 341 are most correlated (blocks 1, 3, 7, and 9 may be included). Then, a correlation operation is performed on nine blocks to determine the position of the most correlated block in one search range 342. In this correlation operation, for example, when the blocks 2 and 8 on both sides are most correlated, it is decided that lateral displacement occurs and a lateral displacement counter counts the displacement. In this way, correlation processing is performed on target data in ROI to calculate a displacement in ROI and a count C of the lateral displacement counter. Since data in ROI is divided by the search range 342, the number A of divided search ranges 342 is also calculated. The displacement in ROI is sent to the elasticity modulus calculating device 340, and the count C of the lateral displacement counter and the number A of divided search ranges 342 are sent to the lateral displacement decision device 338.

The lateral displacement decision device 338 decides the presence or absence of lateral displacement based on the inputted A and C (S46). The decision is made depending upon whether A/X<C is established where X represents an empirically fixed threshold value. When A/X<C is established, it is decided that a force is evenly applied to the subject in the vertical direction. In this case, a lateral displacement flag is set at "0" and stored in the pressing state memory 306 (S47). When A/X<C is not established, it is decided that a force is not evenly applied to the subject in the vertical direction and a living tissue is laterally displaced. In this case, a lateral displacement flag is set at "1" and stored in the pressing state memory 306 (S52). For example, as shown in FIG. 39, the contents of the pressing state memory 306 is indicated as a warning "laterally displaced" on the lower side of the tomographic image 335 (S56).

Meanwhile, the elasticity modulus calculating device 340 calculates distortion data S based on a displacement B measured by the displacement measuring device 339 (S48, S53), and the elastic image constructing section 305 of FIG. 30 performs gradation processing on the distortion data S to construct an elastic image, and displays the elastic image on the display section 303.

Hence, according to the present embodiment, the operator can confirm how the force of the probe is applied to the subject in real time. In the event of lateral displacement, the operator can adjust the operation of the probe in such a manner as to reduce lateral displacement, thereby quickly obtaining a proper elastic image.

INDUSTRIAL APPLICABILITY

As described above, according to the present invention, it is possible to stably form a high-quality elastic image even in an arbitrary time phase during an elastic image diagnosis. Further, according to the present invention, it is possible to stably perform high-quality elasticity imaging with high reliability without being mislead by information on an insignificant elastic image frame having not been removed, and simultaneously it is possible to feed back causes including an improper operating method (pressing method, etc.) to the operator through an elastic image, thereby instantly making search for a pressing method or the like enabling a higher quality image at the site of imaging, and providing a clinically useful ultrasound apparatus keeping its real-time property and simplicity of ultrasound imaging. Moreover, according to the present invention, it is possible to provide the operator pressing operation information for obtaining a proper elastic image, thereby efficiently obtaining an elastic image.

The invention claimed is:

1. An intra-corporeal ultrasound probe which obtains an elasticity image, comprising:
    an insertion part which is inserted into a subject so as to at least face an inner surface of an elasticity image target of an inside of the subject;
    an ultrasound wave transmit/receive section provided on only one portion of a surface of the insertion part so as to transmit an ultrasound wave toward the inner surface of the elasticity image target of the subject and to receive an ultrasound wave of the elasticity image target reflected from the subject; and
    a pressing mechanism which comprises a bag disposed only with respect to the only one portion of the surface of the insertion part for supplying liquid between the inside of the subject and the insertion part, the pressing mechanism expanding and shrinking the bag with respect to the only one portion of the surface of the insertion part utilizing the liquid so as to only apply a pressure to a contact surface at the inner surface of the elasticity image target of the subject in a direction substantially perpendicular to the inner surface of the elasticity image target and to enable the ultrasound wave transmit/receive section to obtain a high-quality elasticity image of the elasticity image target of the subject, the bag being provided outside of the insertion part of an existing transrectal ultrasound probe and fixed to the insertion part with fixing belts provided on opposite sides of the ultrasound wave transmit/receive section along an axial direction of the probe and covering corresponding opposite side portions of the bag.

2. The intra-corporeal ultrasound probe according to claim 1, wherein the bag comprises a first part serving as the ultrasound wave transmit/receive surface at least covering the ultrasound wave transmit/receive section and a second part other than the first part, and
    wherein the second part comprises a shell which is lower in flexibility than the first part and which regulates a moving direction of the first part.

3. The intra-corporeal ultrasound probe according to claim 1, wherein the insertion part of the existing transrectal ultrasound probe includes a cylindrical casing for storing the ultrasound wave transmit/receive section.

4. The intra-corporeal ultrasound probe according to claim 3, further comprising a stopper which is attached at another portion of the surface of the insertion part and acts as a support surface.

5. The intra-corporeal ultrasound probe according to claim 1, further comprising:
    a pressure measuring section for measuring a pressure applied to the contact surface; and
    a pressure control section for controlling the pressing mechanism according to the pressure measured by the pressure measuring section.

6. The intra-corporeal ultrasound probe according to claim 5, wherein the pressure measuring section measures a pressure applied to the contact surface by measuring a pressure of the liquid in the bag.

7. The intra-corporeal ultrasound probe according to claim 1, wherein the pressing mechanism comprises:
    a holding part held by an operator; and
    a control switch which is disposed on a position enabling the switch to be operable with a hand of the operator who holds the holding part and controls the pressing operation of the pressing mechanism.

8. An ultrasound elasticity imaging apparatus, comprising:
    the intra-corporeal ultrasound probe of claim 1;
    the ultrasound wave transmit/receive section including an ultrasound wave transmitting section for outputting an ultrasound signal for driving the ultrasound probe;
    a displacement measuring section which obtains two tomographic image data different in time series from a reflected echo signal received from the ultrasound probe and measures a displacement of each part in the subject based on the two tomographic image data;
    an elasticity calculating section for calculating a distortion or a modulus of elasticity of a tissue of each part in the subject based on displacement data of each part in the subject, the displacement data being measured by the displacement measuring section;
    an image generating section for generating the elasticity image based on a distortion or a modulus of elasticity determined by the elasticity calculating section; and
    a display section for displaying the generated elasticity image.

9. The ultrasound elasticity imaging apparatus according to claim 8, further comprising a pressing period control section for controlling a pressing period of the pressing mechanism according to a time interval of the two tomographic image data.

10. The intra-corporeal ultrasound probe according to claim 1, wherein the liquid is water or physiological saline solution.

11. The intra-corporeal ultrasound probe according to claim 1, further comprising:
    a tube; and
    a pump for changing an amount of the liquid in the bag through the tube.

12. The intra-corporeal ultrasound probe according to claim 4, wherein the support surface provided on the insertion part comes into contact with an opposed contact surface of the subject which is substantially opposed to the inner surface of the elasticity image target of the subject.

13. The intra-corporeal ultrasound probe according to claim 2, wherein the shell is a part of the bag which is made thicker than the other parts of the bag.

14. The intra-corporeal ultrasound probe according to claim 2, wherein the shell is a net which is bonded to a part of the bag.

15. The intra-corporeal ultrasound probe according to claim 1, wherein the pressing mechanism utilizes the liquid to apply the pressure to the contact surface at the inside of the subject substantially only in the direction perpendicular to the surface of the ultrasound wave transmit/receive section.

16. The intra-corporeal ultrasound probe according to claim 1, wherein the insertion part has a substantially cylindrical form, and the ultrasound wave transmit/receive section is provided on a side of the insertion part.

17. An intra-corporeal ultrasound probe which obtains an elasticity image, comprising:

an insertion part which is inserted into a subject so as to at least face an inner surface of an elasticity image target of an inside of the subject;

an ultrasound wave transmit/receive section provided on only one portion of a surface of the insertion part so as to transmit an ultrasound wave toward the inner surface of the elasticity image target of the subject and to receive an ultrasound wave of the elasticity image target reflected from the subject; and a pressing mechanism which comprises a bag disposed only with respect to the only one portion of the surface of the insertion part for supplying liquid between the inside of the subject and the insertion part, the pressing mechanism expanding the bag with respect to the only one portion of the surface of the insertion part utilizing the liquid so as to only apply a pressure to a contact surface at the inner surface of the elasticity image target of the subject in a direction substantially perpendicular to the inner surface of the elasticity image target and to enable the ultrasound wave transmit/receive section to obtain a high-quality elasticity image of the elasticity image target of the subject;

wherein the pressing mechanism expands the bag utilizing the liquid to automatically apply a pressure to the contact surface at the inner surface of the elasticity image target of the subject at a desired constant rate in a fixed direction in order to obtain the elasticity image at a predetermined time.

18. The intra-corporeal ultrasound probe according to claim 1, wherein the pressing mechanism expands the bag utilizing the liquid to automatically apply a pressure to the contact surface at the inner surface of the elasticity image target of the subject at a desired constant rate in a fixed direction in order to obtain the elasticity image at a predetermined time.

19. The intra-corporeal ultrasound probe according to claim 1, wherein at least one of a configuration of the bag and the fixing belts substantially presents expansion of the bag in the axial direction of the probe so that the bag is expandable only in a direction substantially perpendicular to the axial direction of the probe and substantially perpendicular to a surface of the ultrasound wave transmit/receive section covered thereby.

20. The intra-corporeal ultrasound probe according to claim 1, wherein the ultrasound wave transmit/receive section transmits and receives the ultrasound wave through the liquid within the bag so as to obtain the high-quality elastic image of the elasticity image target of the subject.

21. The intra-corporeal ultrasound probe according to claim 2, wherein the shell is formed of a material different from a material of the first part of the bag.

22. The intra-corporeal ultrasound probe according to claim 2, wherein the shell is provided at least at the opposite side portions of the bag along the axial direction of the probe.

* * * * *